(12) United States Patent
Tajima

(10) Patent No.: US 7,473,396 B2
(45) Date of Patent: Jan. 6, 2009

(54) DEVICE FOR CONTAINING, REACTING AND MEASURING, AND METHOD OF CONTAINING, REACTING AND MEASURING

(75) Inventor: Hideji Tajima, Chiba (JP)

(73) Assignee: PSS Bio Instruments, Inc., Livermore, CA (US)

( * ) Notice: Subject to any disclaimer, the term of this patent is extended or adjusted under 35 U.S.C. 154(b) by 1020 days.

(21) Appl. No.: 10/467,361

(22) PCT Filed: Feb. 12, 2002

(86) PCT No.: PCT/JP02/01147

§ 371 (c)(1),
(2), (4) Date: Feb. 9, 2004

(87) PCT Pub. No.: WO02/063300

PCT Pub. Date: Aug. 15, 2002

(65) Prior Publication Data

US 2004/0114890 A1 Jun. 17, 2004

(30) Foreign Application Priority Data

Feb. 9, 2001 (JP) ............................. 2001-034556

(51) Int. Cl.
*G01N 21/64* (2006.01)
(52) U.S. Cl. .............................. 422/57; 422/56; 422/58; 422/82.08; 422/99; 435/287.9; 435/288.7; 436/180
(58) Field of Classification Search ............. 422/57–58, 422/82.08, 99; 435/287.9, 288.7; 436/180
See application file for complete search history.

(56) References Cited

FOREIGN PATENT DOCUMENTS

| JP | 57-171266 A | 10/1982 |
|---|---|---|
| JP | 10-150975 A | 6/1998 |
| JP | 11-125637 A | 5/1999 |
| JP | 11-326339 A | 11/1999 |
| JP | 2001-83158 A | 3/2001 |

OTHER PUBLICATIONS

Japanese Patent Office, "International Search Report," PCT/JP02/01147, Apr. 16, 2002, 2 pages.

*Primary Examiner*—Jill Warden
*Assistant Examiner*—Jyoti Nagpaul
(74) *Attorney, Agent, or Firm*—Haynes and Boone, LLP

(57) ABSTRACT

The invention relates to a device for containing, reacting and measuring, and a method of containing, reacting and measuring, and provides a device for containing, reacting and measuring, and a method of containing, reacting and measuring which is also able to effectively and quickly perform the reaction processing, measuring and identification.

The invention comprises; a transparent container section having a liquid inlet/outlet and which is able to contain a base member with several kinds of substances for detection having predetermined chemical structures fixed at respective fixed positions which are arranged at predetermined spacing, and with each of the chemical structures associated with each of the fixed positions, a drawing and discharging section which is able to draw and discharge the liquid into and from the container section via the inlet/outlet, and a measuring device which is able to receive light from the contained base member, external to the container section and in a condition associated with the fixed position.

5 Claims, 16 Drawing Sheets

DEVICE FOR CONTAINING, REACTING AND MEASURING, AND METHOD OF CONTAINING, REACTING AND MEASURING

This application is a national phase of filing of international application No. PCT/JP02/01147, filed Feb. 12, 2002, which claims priority to Japanese patent application No. 2001-034556, filed Feb. 9, 2001.

TECHNICAL FIELD

The present invention relates to a device for containing, reacting and measuring, and a method of containing, reacting and measuring. The invention relates to all manner of fields which require the handling of low molecular weight organisms and biopolymers such as genes, immune systems, amino acids, proteins and sugars, including for example the fields of engineering, agricultural science incorporating foodstuffs, agricultural production and seafood processing, pharmaceuticals, the medical field incorporating hygiene, health, immunity, disease and genetics, and scientific fields such as chemistry and biology.

In particular, the present invention relates to a device for containing, reacting and measuring and a method of containing, reacting and measuring which is suitable for the analysis of genes including mutational analysis, polymorphic analysis, mapping, base sequence analysis, and mechanism analysis.

BACKGROUND ART

Currently, when determining gene base sequences a DNA chip is used.

This DNA chip is a flat sheet comprising a semiconductor film or a slide glass on to which is spotted a minute quantity of suspensions of a large number of different, known oligonucleotides, with the oligonucleotides fixed in an array pattern sequence. The DNA chip is made by using a pipette apparatus in order to form a plurality of the oligonucleotides on the restricted surface thereof, minute quantities of oligonucleotide suspensions being dispensed spot by spot on to the surface while leaving a predetermined separation between adjacent spots to prevent mixing. By using such a DNA chip, various assay or analysis related to genes is performed.

For example, in determining the base sequence of an unknown target gene, conventionally the user pours a liquid with the target genetic material suspended therein and which is labeled with a luminescent material, onto the DNA chip. Then after leaving for a fixed reaction time, the surplus suspension is removed by washing. Subsequently, the luminescence from the DNA chip is detected to thereby determine the base sequence from the position where the luminescence is detected.

However, in order to manufacture the DNA chip, with the arrangement of a large number of different oligonucleotides at a high density in a plane on a restricted region, not only is there the likelihood of cross-contamination occurring due to these becoming close to each other, but also the oligonucleotides at each of the fixed positions becomes an even smaller amount. In particular, if the oligonucleotides at each of the fixed positions becomes a small amount, determining the luminescence position is susceptible to error so that there is a problem with accuracy.

Furthermore, heretofore a DNA chip with substances such as oligonucleotides fixed to the plane surface of for example a glass plate of a prepared slide of a size of for example approximately 2.6 cm×7.6 cm is used. In supplying a liquid to this substance such as the oligonucleotide which is at the fixed positions on the plane surface, a method is used where liquid of around several 10 μliters is dispensed onto the plane surface, and then the glass plate or a film is mounted in a sandwich condition on the flat surface by hand, so that a uniform thin liquid layer is formed to supply a small amount of liquid evenly to the respective fixed positions. With this method, the step for mounting the film or the like is necessary, and hence this becomes an obstacle to automation of the operation. Moreover, fluidization of the liquid for supply in order to supply the liquid by mounting the film or the like, is problematic. Furthermore, due to miniaturization there are problems in that the encounter characteristics or reactivity of the target substance are more and more reduced, so that processing takes time, and for the processing a high density liquid is necessary.

Moreover, since the sample is arranged in a plane, then with higher densities, the handling and automation thereof is even more difficult. Consequently, the manufacture of the DNA chip requires a considerable amount of effort and time, resulting in high cost. In particular, in performing analysis, assay or determination of the structure of large amounts of unknown target substances which contain base sequences, the analysis, assay etc. of a large amount of DNA chips is necessary. Therefore, the present applicant in order to solve this problem has disclosed in Japanese patent applications (Un-published Japanese Patent Application Nos. 2000-7763, 2000-37273, 2000-77144, not yet published at the time of this application), an integrated support which has one, or two or more long slender base members of for example filaments, fibers, tapes, or rods, and a variety of substances for detection of predetermined chemical structures which are lined up and fixed along the longitudinal direction of the base member, the base member being wound, laminated or formed in a row, so that the fixed locations of each type of substance for detection is associated with the chemical structure thereof.

However, even though the manufacture of such an integrated carrier is simplified and the cost reduced, there is a problem in that if reaction, measuring and identification using such an integrated carrier cannot also be performed efficiently and quickly, the advantage of this integrated carrier cannot be sufficiently realized.

Therefore, the present invention aims to resolve the problems outlined above, with a first object of providing a device for containing, reacting and measuring and a method of containing, reacting and measuring, which is able to effectively and quickly perform reaction, measuring and identification not only for the aforementioned integrated carrier but also including DNA chips.

A second object of the present invention is to provide a device for containing, reacting and measuring and a method of containing, reacting and measuring, which can consistently and automatically perform reaction, measuring, and identification of a substance for detection or a bonding substance.

A third object of the present invention is to provide an easily operated device for containing, reacting and measuring and a method of containing, reacting and measuring which can perform reaction, measuring, and identification using a minute amount of liquid in which is suspended a labeled bonding substance.

A fourth object of the present invention is to provide a highly reliable device for containing, reacting and measuring, and a method of containing, reacting and measuring which can perform accurate identification of a substance for detection or a bonding substance.

A fifth object of the present invention is to provide an integrated carrier where reaction, measuring and identification is further simplified.

DISCLOSURE OF THE INVENTION

In order to solve the above technical problems, a first aspect of the invention is an integrated carrier having a base member of a long and slender shape such as a filament, a braid, or tape, with several kinds of substances for detection having predetermined chemical structures fixed thereto at predetermined spacing along a longitudinal direction thereof with each of the chemical structures associated with their fixed positions, wherein the base member is integrated by winding, laminating or being formed in a row, in a state with the fixed positions measurable from the outside.

Here the "substance for detection" is a chemical substance which is recognized by the specific bonding, and is obtained by bonding. For example this is a chemical substance including biopolymers such as nucleic acid, proteins, amino acids, sugars, and peptides, and low molecular weight organisms. As the nucleic acid, there is double strand DNA or single strand DNA. The bonding substance is a chemical substance having bondability with the substance for detection. For example, this is a chemical substance such as a biopolymer of for example nucleic acid, proteins, sugars and peptides, or a low molecular weight organism. The substance for detection or the bonding substance may be for example a natural molecule or an artificial molecule. In the present invention, the contact surface characteristics of the substance for detection and the bonding substance having connectivity with the substance for detection are mutually complimentary. This is used for determining the structure of the target substance, various kinds of assay, or for analyzing. For example, this is genetic material of oligonucleotides, and immunity substances. Genetic material includes nucleic acid (polynucleotide), oligonucleotides of decomposition products, nucleotides and so forth. Here, "base member" is formed from a flexible material or a non flexible material. This material may be for example an organic material such as polyethylene, polystyrene, polypropylene, urethane, an inorganic material such as glass fiber, ceramics, metal, or a material where organic and inorganic materials are combined such as where fine ceramics particles are spread all over a film or tape of an organic material. The organic material includes not only artificial material but also includes natural material such as silk, cotton and the like. Furthermore the base member, may be formed, at least in each fixed position, from various types of porous material, foam material, fibrous material, or irregular surface material.

In the present invention, "the fixed positions are wound in a state measurable from the outside, or are laminated, or formed in a row". Therefore, for example the base member is made in a three dimensional shape so as to be measurable. As a result, the measurable area of the substance for detection is increased so that measurement from the outside can be reliably performed, and reliability thus increased. For example, in the case where the base member is opaque or translucent, then so that not only the outermost surface of the base member but also the side face of the base member is measurable, fixing is performed so as to surround the periphery in the circumferential direction along a direction perpendicular to the longitudinal direction of the base member, and the base member is wound or laminated or formed in a row to open up a space between the base members. As a result, even if the base member is wound twisted or laminated, or formed in a row, the fixed positions can be measured from the outside.

Preferably fixing is performed to a transparent or translucent base member. Moreover, the respective fixed positions may be measured three dimensionally by providing light receiving sections at two different positions so as to be able to receive light in different directions, and viewing stereoscopically. Furthermore, while preferably the base member is usually wound as only one layer, in the case where the transparent or translucent base member is measured stereoscopically, then this can be wound in a number of layers.

For the integrated carrier, there may be provided a carrier with the base member wound or laminated or formed in a row. As a result, in the case where the base member is a flexible material, then the positioning can be easily and positively performed. However, if the base member is a non flexible material, then the carrier is not really necessary.

Furthermore, "chemical structure" is a molecular structure of the substance for detection or bonding substance. For example in the case where the substance for detection is a genetic material, this is a base sequence. Regarding "wound base member", for example preferably the carrier is provided and united and held by inserting the edges of the base member in a space provided on the carrier, and fixing by frictional force.

Furthermore, regarding the integrated carrier, when this is contained in a container section described later, preferably this has a construction such that a space is formed with the inner wall of the container section so that liquid can flow smoothly therethrough. As a result, when the liquid is drawn, the liquid can be reliably contacted with the substance for detection, and when the liquid is discharged, the liquid can pass smoothly between the integrated carrier and the inner wall, leaving no residual liquid.

Moreover, when the integrated carrier or the base member are contained in the container section, it is necessary to fix the position of the integrated carrier and the base member inside the container section so that these do not move inside the container section due to movement of the container section.

As such a construction, for example for the integrated carrier there is provided a carrier (for example cylindrical or prismatic shape) on which the base member is wound, laminated or formed in a row. This may be realized by providing on the carrier, a protective portion for preventing contact of the base member with the inner wall of the container (also including a later described container section) for containing the integrated carrier. The protective portion is preferably one where a protruding portion having a height exceeding the thickness of the wound base member and with a tip thereof for contact with the container inner wall, is provided for example on a suitable part (for example opposite rim portions, opposite end portions etc.) of the carrier (for example cylindrical or prismatic shape), protruding from the surface of the carrier (for example in the radial direction).

Moreover, preferably the contact point of the protective portion with the container inner wall is formed so as to have a minimal area. This is because if the area of the contact point is large, the amount of residual liquid is likely to increase. The shape of the protective portion is formed so that flow of liquid inside the container portion does not become impossible due to the presence of the protective portion. This situation is avoided for example by providing cutouts in an annularly formed protruding portion, or by providing pin-like protruding portions. By means of this protective portion, the positioning of the integrated carrier inside the container portion can also be performed.

Furthermore, in the case where minute quantities of liquid are handled, the carrier is preferably formed as a solid. Moreover, preferably the spacing between the base member and the inner wall of the container is as small as possible. On the other hand, in the case of handling relatively large quantities of liquid, the carrier is preferably formed from a hollow and/or porous member.

Furthermore, in the surface of the supporting medium where the base member is wound, laminated, or formed in a row, there may be provided corrugations, or grooves of a helical shape for example, or stripes, so that by winding or laminating the base member or forming this a row, along the corrugations or grooves or stripes, or so as to cut the corrugations or grooves or stripes transversely, a space is opened up between the base members, so that a space is provided between the support medium and the base member, so that liquids can circulate easily therethrough.

With this aspect of the invention, according to the first aspect of the invention, since the base member is wound so that each of the fixed positions of the base member are able to be measured from the outside, measuring or detection of the labels for the labeled fixed positions can be performed easily and accurately from outside. Consequently, if this integrated carrier is used, then at the time of performing reaction as well as measurement, handling is simplified, and consistent processing can be performed.

Regarding "predetermined spacing", in the case of assay or analysis where it is necessary to avoid contact between the adjacent substances for detection, then the fixed amount of the substances for detection, and there spread is considered, and this is a distance exceeding their spread. In the case of assay or analysis where it is not necessary to avoid contact between the adjacent substances for detection, then this may be a distance such that the spreads overlap.

A second aspect of the invention is device for containing, reacting and measuring wherein this has; a transparent container section having a liquid inlet/outlet and which is able to contain a base member with several kinds of substances for detection having predetermined chemical structures fixed at respective fixed positions which are arranged in a predetermined spacing, and with each of the chemical structures associated with each of the fixed positions, a drawing and discharging section which is able to draw and discharge the liquid into and from the container section via the inlet/outlet, and a measuring device which is able to receive light from the contained base member, external to the container section and in a condition associated with the fixed position.

Since the container section has a liquid inlet/outlet, the base member as well as liquid can be contained in the container section. As a result, reaction between the substance for detection of the base member and the bonding substance contained in the liquid is possible inside the container section. The container section has a container opening for containing the base member. This container opening may also be used for example for connection to the drawing and discharging section.

Here the base member need not necessarily be a long and slender shape. Moreover, a long and slender base member which is wound around the integrated carrier is also possible. Furthermore, this may be for example a planar DNA chip. "Arranged (at predetermined spacing)" is so that the respective fixed positions can be measured from the outside. For example, in the case where the base member is long and slender, this is the condition where each fixed position is generally arranged along the length of the base member, while in the case where the base member is planar, this is the condition where each fixed position is arranged in matrix form.

Furthermore, the shape or size of the container section may be made a shape or size close to the shape or size of the base member (or the integrated carrier), based on the shape or size of the base member (or integrated carrier), so that the space between the container inner wall and the base member is made narrow, enabling small quantities of liquid to be handled. Moreover, even if the base member is long and slender, for example a filament or a braid, it is not necessary for the material to have flexibility, and a non flexible material such as a wire or a bar is suitable. Furthermore, one where a non flexible base member is formed in a coil is also suitable.

According to the second aspect of the invention, reaction or washing can be performed with the same or a different liquid by drawing or discharging the necessary liquid into or from the container section with the base member contained in the container section, and in this condition measurement can also be performed. Consequently, processes such as reaction, measurement and the like can be performed efficiently and consistently, by a quick and a simple operation. Furthermore, since the various processes can be performed with the base member contained in the container section, cross-contamination is prevented so that reliability is high. Moreover, by determining the shape or size of the container section based on the shape or size of the base member, processing can also be performed with minute quantities of liquid.

A third aspect of the invention is a device for containing, reacting and measuring, wherein the measuring device has a light receiving section for receiving light from the base member, and a scanning section for relatively moving the light receiving section or the container section and scanning each fixed position of the base member. The scanning section may move the light receiving section, or may move the container section.

According to the third aspect of the invention, by scanning the base member, light from the base member can be received without leakage, and hence reliability of the measurement results is high.

A fourth aspect of the invention is a device for containing, reacting and measuring wherein the container section is removably mounted on a nozzle section provided in the drawing and discharging section.

According to the fourth aspect of the invention, since the container section for contacting the liquid with the base member is removably mounted, then by replacing container sections, cross-contamination can be reliably prevented. Furthermore, by providing a magnetic force device external to the container section, or by replacing the container section with a pipette section provided with a magnetic force device which can perform separation by attaching magnetic particles to the inner wall, then this can be used in common with a device which uses magnetic particles, and hence many kinds of processing can be performed even more efficiently and consistently.

A fifth aspect of the invention is a device for containing, reacting and measuring wherein this further has a moving section which is capable of relatively moving between the inlet/outlet and a processing area where externally provided containers or the like are mounted.

According to the fifth aspect of the invention, by providing the moving section which relatively moves between the inlet/outlet of the container section and the processing area, processing can be automatically and consistently performed by moving the base member with the base member contained in the container section.

A sixth aspect of the invention is a device for containing, reacting and measuring wherein this further has an identification section for performing identification related to the bonding substance or substance for detection by relatively scanning with the measuring device an area containing all fixed positions of the base member which have been formed by combining labeled bonding substances, labeled by labeling substances which are able to bond with the substance for detection, with substances for detection, and obtaining qualitative and quantitative information related to the labeling substances in the respective fixed positions.

Here "qualitative and quantitative information related to the labeling substance" is information related to the labeling substances produced as a result of reaction. For example this is the kind of the labeling substance, the amount thereof, or the molar ratio. Identification of each fixed position is performed for example by a mark (luminescent material, coloration etc.) provided at a constant period on the base member. The mark may be configured so as to represent a standard strength of the emission intensity. As a result, the quantitative information can be reliably obtained. As a labeling section, a display section may be provided for displaying the obtained information or identification contents on a screen.

According to the sixth aspect of the invention, by scanning the base member, the light from the base member can be received without leakage. Therefore reliability of the measurement results is high.

A seventh aspect of the invention is a device for containing, reacting and measuring wherein the base member is formed in a long and slender shape such as a filament, a braid or a tape, and the several kinds of substances for detection are fixed at predetermined spacing along a longitudinal direction thereof, and in the case where the base member is contained in a linearly extended condition, the container section is a slender tube, and the base member is contained with the longitudinal direction thereof along the axial direction of the slender tube, and the size and shape of the slender tube is determined based on the size and shape of the base member, and the measuring device measures by relatively scanning along the axial direction of the slender tube.

Here "slender tube" may be a disposable one which is provided so as to be removable with respect to the drawing and discharging section.

According to the seventh aspect of the invention, since the base member is contained in an extended condition, specifying of each fixed position is simple and accurate.

An eighth aspect of the invention is a device for containing, reacting and measuring wherein the base member is formed in a long and slender shape such as a filament, a braid, or a tape, with several kinds of substances for detection having predetermined chemical structures fixed at predetermined spacing along the longitudinal direction thereof, with each chemical structure associated with the fixed positions thereof, and in the case where the base member forms an integrated carrier, the container section comprises; a large diameter section for containing the integrated carrier and a small diameter section having an inlet/outlet at a tip end and capable of insertion into an external container, and the drawing and discharging section draws and discharges the liquid into and from the large diameter section via the inlet/outlet, and the size and shape of the container section is determined based on the size and shape of the integrated carrier, and the measuring device is one for receiving light from the base member external to the large diameter section.

According to the eighth aspect of the invention, by determining the size and shape of the container section based on the size and shape of the integrated carrier, and making the space between the integrated carrier and the inside wall of the container section narrow, processing such as reaction can be performed even with a small quantity of liquid, thus simplifying handling. Furthermore, according to this aspect of the invention, since the base member is integrated and contained as an integrated carrier, measurement can be performed in relation to numerous fixed positions, and hence analysis of complicated structures can also be efficiently performed.

A ninth aspect of the invention is a device for containing, reacting and measuring wherein the light receiving section of the measuring device is provided inside a light shielding box, and the light shielding box has a box body, and a cover provided so as to cover an opening of the box body, and has an opening provided in the cover to allow the container section to pass therethrough in order to insert the container section into the box body, and a closure device which covers the opening to form a closure space with the container section inserted into the box body. As well as the light receiving section, the illumination section may also be provided inside the light shielding box. Furthermore, the light receiving section provided inside the light shielding box may be only a photodetector, or this may include electrical circuits belonging to this, or a measuring device body.

According to the ninth aspect of the invention, since light reception is performed inside the light shielding box, noise of light from outside is shut off, and light does not leak to the outside. Hence there are no adverse effects on other measurements, enabling measurements of high reliability to be performed, and since a plurality of measurements can be performed concurrently in an integrated condition, the efficiency is even higher.

A tenth aspect of the invention is a device for containing, reacting and measuring wherein the integrated carrier is contained in a condition with the base member positioned so as not to come in contact with an internal surface of the container section.

To achieve this, for example, the abovementioned protective section may be provided on the integrated carrier.

According to the tenth aspect of the invention, the base member is positioned so as not to come in contact with the internal surface of the container section. Consequently, sufficient contact is possible between the base member and the liquid, and when discharging liquid, a situation where liquid remains in the space between the base member is prevented. Moreover since the base member is positioned, reliable measurement can be performed.

An eleventh aspect of the invention is a method of containing, reacting and measuring having: a containing step for containing in a transparent container section, a base member of a long and slender shape such as a filament, a braid, or tape, with several kinds of substances for detection having predetermined chemical structures fixed thereto at predetermined spacing along a longitudinal direction thereof, and with each of the chemical structures associated with their fixed positions; a reaction step for drawing a liquid suspending a labeled bonding substance to inside the container section and immersing the base member in the liquid to react the bonding substance with the substance for detection; a measurement preparation step for removing any bonding substances which have not contributed to the reaction and the liquid; and a measurement step for measuring light from the base member contained in the container section. "Removal" in the "measurement preparation step" is performed for example by washing using a washing solution. Washing is more effectively performed by repeated drawing and discharging of the washing solution or by agitating. Furthermore, in preparation for measurement, the interior of the container section is completely dried, or this is performed by drawing up a liquid for measurement as described later.

According to the eleventh aspect of the invention, reaction or washing is performed by drawing up or discharging a necessary liquid into and out of the container section with the base member contained in the container section, with respect to the same or different liquids. In this condition, measurement can also be performed. Consequently, processes such as reaction and measuring can be efficiently and consistently carried out with a prompt and simple operation. Furthermore, several kinds of processing can be performed while contained in the container section. Therefore cross contamination can be prevented so that reliability is high. Moreover, by setting the shape or the size of the container section based on the shape or the size of the base member, the processing can be performed with a very small quantity of liquid.

A twelfth aspect of the invention is a method of containing, reacting and measuring wherein the measurement step scans all fixed positions of the base member by relatively moving the container section or a light receiving position.

According to the twelfth aspect of the invention, by scanning the base member, the light from the base member can be received without leakage. Therefore reliability of the measurement results is high.

A thirteenth aspect of the invention is a method of containing, reacting and measuring wherein in the measurement preparation step there is included a step for drawing measurement liquid after removing any bonding substances which have not contributed to reaction and liquid suspending these, and the measurement step measures in a condition with the base member immersed in the measurement liquid. Here for the "measurement liquid" it is preferable to use for example distilled water, or a liquid which has a refractive index close to the refractive index of the material constituting the container section. As a result, scattering of unnecessary light which interferes with measurement can be prevented.

According to the thirteenth aspect of the invention, instead of removing the bonding substances which have not contributed to the reaction and the liquid suspending these, the measurement liquid is drawn so as to immerse the base member. Consequently, by filling a liquid having for example a predetermined refractive index close to the refractive index of the material constituting the container section, between the container section and the base member, reflection or refraction or distortion produced at the interface between the container section and air can be prevented, thus giving clarity and enabling accurate measurement to be performed.

A fourteenth aspect of the invention is a method of containing, reacting and measuring wherein in the reaction step, the container section or liquid which is drawn into the container section is shaken, or drawing and discharging of the liquid is repeated. Furthermore, temperature control inside the container section may be performed in the reaction step, by this shaking or drawing and discharging operation, and/or instead of this shaking or drawing and discharge operation, by drawing up into the container section, from a container which contains a liquid in a constant temperature condition which is held at a predetermined temperature by a thermostat, liquid of the constant temperature condition, or by repeating the drawing/discharge operation with respect to the container section.

According to the fourteenth aspect of the invention, by shaking the container section or the liquid contained in the container section, and repeating the drawing and discharging of the liquid, the encounter characteristics between the bonding substance suspended in the liquid and the substance for detection of the base member can be increased so that the reaction can be promoted.

A fifteenth aspect of the invention is a device for containing, reacting and measuring, wherein the base member contained in the container section is integrated to form an integrated carrier, and the measuring device has a light receiving section which receives light from the integrated carrier, and a scanning section which rotates the integrated carrier or the container section containing the integrated carrier about the axis thereof.

Here the light receiving section is for example one provided with an optical sensor on the outside of the container section following along parallel with the axial direction of the nozzle section, so as to be able to receive light from the integrated carrier. Furthermore, an optical filter may be provided on the end portion on the container section side of the light receiving section.

According to this aspect of the invention, rather than moving the measuring device body for scanning, the container section side is rotated. Consequently, by limiting the object of the translational movement and rotation movement to the container section side, and fixedly providing the measuring device body, the overall apparatus configuration and control can be simplified, and an improvement in efficiency achieved. Furthermore, scanning can be performed with minimum operations.

A sixteenth aspect of the invention is a device for containing, reacting and measuring wherein the containing section is removably mounted on a nozzle section having the drawing and discharging section, and the scanning section rotates the containing section by rotating the nozzle section with respect to the axis thereof.

According to the sixteenth aspect of the invention, since the container section is removably mounted on the nozzle section which is rotationally driven, the construction of the container section can be simplified, and a similar effect to that described for the fourth aspect of the invention is demonstrated.

A seventeenth aspect of the invention is a device for containing, reacting and measuring further having a moving section capable of relatively moving between the inlet/outlet, and processing areas where externally provided containers or the like are mounted, or the light receiving section.

According to the seventeenth aspect of the invention, a similar effect to that described for the fifth aspect of the invention is demonstrated.

An eighteenth aspect of the invention is a device for containing, reacting and measuring further having an identification section which scans the region containing all the fixed positions by the measuring device, by rotating the container section containing an integrated carrier formed by bonding to the substance for detection a bonding substance labeled with a labeling material, being a material capable of bonding with the substance for detection, and obtains qualitative and quantitative information related to the labeling substance in the respective fixed positions, and performs identification in relation to the bonding substance or substance for detection.

As a labeling section, a display section may be provided for displaying the obtained information or identification contents on a screen.

According to the eighteenth aspect of the invention, a similar effect to that described for the sixth aspect of the invention is demonstrated.

A nineteenth aspect of the invention is a device for containing, reacting and measuring wherein the integrated carrier has a base member of a long and slender shape such as a filament, a braid or a tape with predetermined substance for detection fixed thereto at a predetermined spacing along the longitudinal direction thereof, with each of the substances for detection associated with their fixed positions, and a cylindrical carrier with the base member wound therearound, and the container section comprises; a large diameter section for containing the integrated carrier and a small diameter section having an inlet/outlet at a tip end and capable of insertion into an external container, and the drawing and discharging section draws and discharges the liquid into and from the large diameter section via the inlet/outlet, and the size and shape of the container section is determined based on the size and shape of the integrated carrier, and the measuring device is one for receiving light from the base member external to the large diameter section. Here the "cylindrical carrier", may be a solid or hollow. Moreover, this may be such that a groove, corrugation, or longitudinal stripe is provided in the cylindrical carrier so that liquid can flow therealong. "Winding" is performed for example so that the base member becomes approximately perpendicular to the axial direction of the cylindrical carrier. According to this aspect of the invention, a similar effect to that described for the eighth aspect of the invention is demonstrated. Furthermore, since this is wound on the cylindrical carrier, the fixed positions are lined up in a cylindrical shape, making measurement easier.

A twentieth aspect of the present invention is a device for containing, reacting and measuring wherein the cylindrical carrier is contained in the container section such that the central access thereof coincides with the central axis of the nozzle section. As a result, differences in the optical power due to rotation, or fluctuations do not occur so that stabilized and accurate data can be obtained.

A twenty first aspect of the present invention is a device for containing, reacting and measuring wherein the measuring device is further provided with an irradiation section which irradiates a predetermined light onto a region of the integrated carrier so that the light receiving section receives light.

As a result, a labeling substance such as a fluorescent substance which requires excitation light for light emission, can be used.

A twenty second aspect of the invention is a device for containing, reacting and measuring wherein the light receiving section or irradiation section has a large number of optical fibers, and an optical fiber support section which supports the optical fibers in a bundle, and tip portions of the optical fibers are arranged in column form along an axial direction of the nozzle.

Here "column form" includes not only the case of a single row but also includes the case of a plurality of rows. According to this aspect of the invention, a large number of fixed positions along the axial direction can be detected at a time, and hence efficiency is increased.

A twenty third aspect of the invention is a device for containing, reacting and measuring wherein the light receiving section or the irradiation section has fiber glass and a fiber glass support section which supports the fiber glass, and the container section side face of the fiber glass is formed in an oblong shape along the axial direction of the nozzle. According to this aspect of the invention, a large number of fixed positions along the axial direction can be detected at a time, and hence efficiency is increased.

A twenty fourth aspect of the present invention is a device for containing, reacting and measuring wherein on at least one of the inside face or the outside face of the container section, over the whole periphery thereof, a large number of converging optical systems for converging light from the integrated carrier are formed in an array on the ends of the light receiving sections which are provided on the outside of the container section. Here "converging optical system" is for example a cylindrical lens having a generatrix parallel to the axial direction of the installed nozzle section, and having a refractive effect in a plane perpendicular to the generatrix. For the cylindrical lens, preferably this is formed integral with the container section. According to this aspect of the invention, high intensity light emission can be measured.

A twenty fifth aspect of the invention is a method of containing, reacting and measuring comprising: a containing step for containing in a transparent container section, an integrated carrier having a base member of a long slender shape such as a filament, a braid or a tape with several kinds of substances for detection having predetermined chemical structures fixed thereto at predetermined spacing along the longitudinal direction thereof, and with each of the chemical structures associated with their fixed positions, wound on a carrier in a condition where this can be measured from the outside; a reaction step for drawing a liquid suspending a labeled bonding substance which is capable of bonding with the substance for detection, to inside the container section, and immersing the integrated carrier in the liquid to react the bonding substance with the substance for detection; a measurement preparation step for removing the bonding substances which have not contributed to the reaction and the liquid; and a measurement step for measuring light from the base member contained in the container section.

According to this aspect of the invention, a similar effect to that described for the second aspect of the invention or the eleventh aspect of the invention is demonstrated.

A twenty sixth aspect of the invention is a method of containing, reacting and measuring, wherein the measuring step scans all fixed positions of the integrated carrier by rotating the container section or nozzle section. Here "rotating the container section" is performed for example by rotating the container section itself, or the nozzle section on which the container section is removably mounted. For the container section, it is necessary that the integrated carrier is fixed to the container section or the nozzle section so as to faithfully follow the rotation.

According to this aspect of the invention, by limiting the object of not only translational movement but also rotational movement, to the container section side (or the nozzle section), the overall apparatus configuration and control can be simplified and an improvement in efficiency achieved. Furthermore, scanning can be performed with minimum operations.

A twenty seventh aspect of the invention is a method of containing, reacting and measuring wherein in the measurement preparation step, there is included a step for drawing measurement liquid after removing the bonding substances which have not contributed to the reaction and liquid suspending these, and the measurement step measures in a condition with the integrated carrier immersed in the measurement liquid. According to this aspect of the invention, a similar effect to that described for the thirteenth aspect of the invention is demonstrated.

A twenty eighth aspect of the invention is a method of containing, reacting and measuring wherein in the reaction step, the container section or the liquid which is drawn into the container section is shaken, or drawing and discharging of the liquid is repeated. Furthermore, temperature control inside the container section may be performed in the reaction step, by this shaking or drawing and discharging operation, and/or instead of this shaking or drawing and discharge operation, by drawing up into the container section, from a container which contains a liquid in a constant temperature condition which is held at a predetermined temperature by a thermostat, liquid of the constant temperature condition, or by repeating the drawing/discharge operation with respect to the container section. According to this aspect of the invention, a similar effect to that described for the fourteenth aspect of the invention is demonstrated.

A twenty ninth aspect of the invention is a method of containing, reacting and measuring, wherein a device for containing, reacting and measuring having; a nozzle section rotatably provided with respect to a central axis, a transparent container section capable of containing thereinside an integrated carrier removably mounted on the nozzle section with several kinds of objects for detection fixed at predetermined spacing, and having an inlet/outlet for a fluid on the tip end, and a light receiving section for receiving light from the integrated carrier provided along a parallel direction to the axial direction of the nozzle section, on the outside of the container section, uses an optical measuring device, the method having; a reaction step for drawing a liquid suspending a bonding substance which is capable of bonding with the substance for detection, via an inlet/outlet of the container section which contains the integrated carrier, and immersing the integrated carrier in the liquid to react the bonding substance with the substance for detection; a measurement preparation step for removing the bonding substances which have not contributed to reaction and the liquid, and drawing a measurement reagent to said container section; and a measurement step for detecting light emission on the integrated carrier by the light receiving section, from outside of the container section while rotating the nozzle section.

According to this aspect of the invention, a similar effect to that described for the twenty sixth aspect of the invention is demonstrated.

A thirtieth aspect of the invention is a method of containing, reacting and measuring wherein the reaction step is performed by moving the nozzle section with the container section mounted thereon to the position of a container which contains an appropriate reagent, and drawing up this reagent, and the measurement step is performed by moving the nozzle section as far as the position where the light receiving section is provided.

According to this aspect of the invention, even if only the nozzle section is moved, various processing can be performed. Therefore control can be made more efficient with a simple control.

BEST MODE FOR CARRYING OUT THE INVENTION

A description is given of a device for containing, reacting and measuring, and method of containing, reacting and measuring according to embodiments of the present invention, based on the drawings. The description of the embodiments is not to be interpreted as limiting the present invention unless particularly specified.

Figure 1:
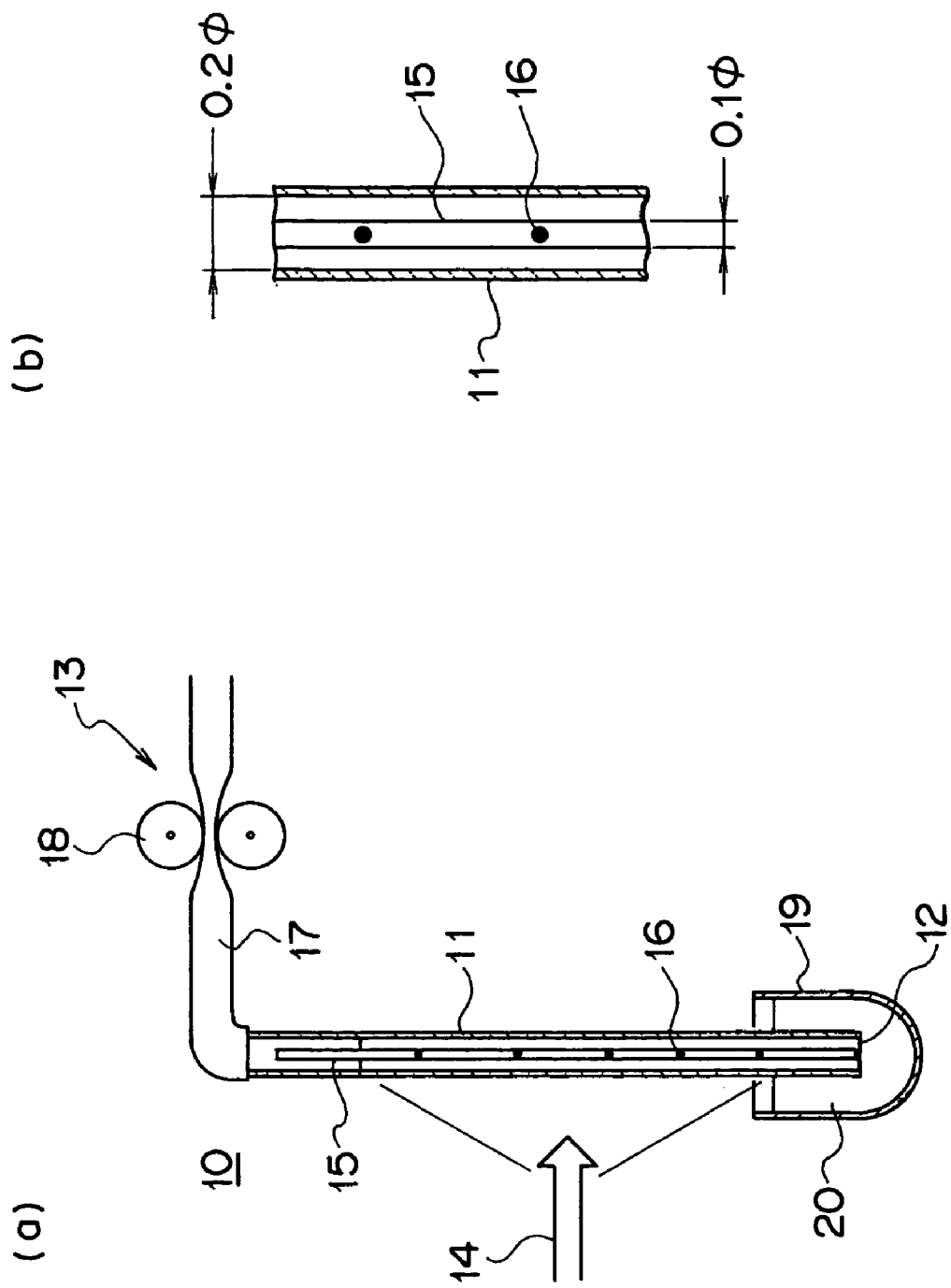
FIG. 1 is a schematic diagram of a device for containing, reacting and measuring according to a first embodiment of the present invention.

FIG. 1(a) shows a device for containing, reacting and measuring 10 according to a first embodiment.

The device for containing, reacting and measuring 10 according to this embodiment has a transparent slender tube 11 serving as the container section and having a liquid inlet 12, a pump 13 connected to the slender tube 11 and serving as a drawing and discharging section for drawing and discharging liquid into and from the slender tube 11, and a light receiving and irradiating section 14 of a measuring device. Inside the slender tube 11 it is possible to contain a liquid, and a base member 15 immersed in the liquid.

The base member 15 is formed in a long and slender shape, and detection substances such as for example oligonucleotides having already known various base sequences are arranged so as to be lined up at predetermined spacing along the longitudinal direction thereof. The base member 15 is contained inside the slender tube 11 in an extended and secured condition so as to adhere to the slender tube 11. Here, reference symbol 16 shows where labeled bonding substances being target substances, bond to the substance for detection to thereby label fixed positions thereof. By analyzing these labeled fixed positions, the unknown chemical structure of the target substance can be determined.

The pump 13 has a tube 17 made from a resilient body and communicated with the slender tube 11, a pressing section 18 for pressing and contracting the tube 17, and a switching valve (not shown in the figure). The pump 13 draws and discharges into and from the slender tube 11, liquid 20 contained in a container 19 provided external to the device for containing, reacting and measuring 10. In the liquid 20 is suspended a target substance which has been labeled by a fluorescent substance or the like (not shown in the figure).

The light receiving and irradiating section 14 is one for shining an excitation light beam for exciting the fluorescent substance, and receiving the produced fluorescence. A scanning section (not shown in the figure) which is moved for scanning, is provided along the slender tube 11.

The shape and size of the slender tube 11 is determined based on the shape and size of the base member 15, and is preferably a size and shape such that the base member 15 can be easily contained inside the slender tube 11 with a margin, and so that a gap produced between the inner wall of the slender tube 11 and the surface of the base member 15 is small to the extent that the base member 15 is easily wetted with a small amount of liquid. As shown in FIG. 1(b), in order to satisfy this condition, the size of the diameter of the slender tube 11 is suitably approximately two times the size of the width or the diameter of the base member 15, and for example in the case where the diameter of the base member 15 is approximately 0.1 mm, then preferably the diameter of the slender tube 11 is for example approximately 0.2 mm.

Figure 2:
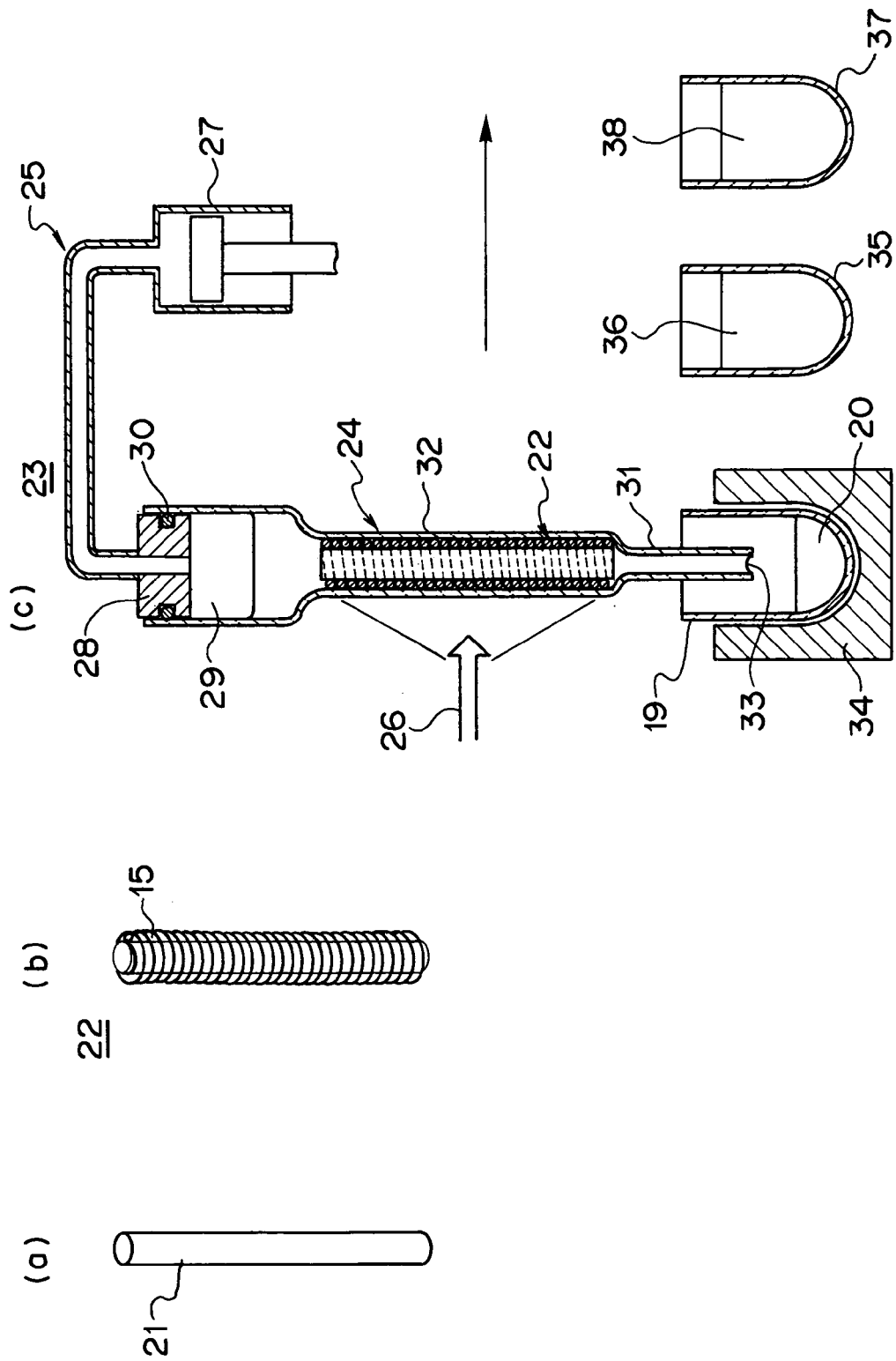
FIG. 2 is a schematic diagram of a device for containing, reacting and measuring according to a second embodiment of the present invention.

Next, FIG. 2 shows a device for containing, reacting and measuring according to a second embodiment.

FIG. 2(a) shows a core 21 serving as a rod shape or cylindrical shape carrier for carrying the aforementioned base member 15 wound around the surface thereof. FIG. 2(b) shows an integrated carrier 22 with the beforementioned base member 15 wound thereon. Here the diameter of the core 21 is for example from approximately 2 to 4 mm, while the thickness of the base member 15 is from approximately 0.05 mm to 0.2 mm, and the length of the base member 15 is for example from approximately 500 mm to 3000 mm. FIG. 2(c) illustrates a device for containing, reacting and measuring 23, and a method of containing, reacting and measuring according to the second embodiment.

The device for containing, reacting and measuring 23 has a pipette section 24 serving as the container section, a drawing and discharging section 25 for drawing and discharging into and from the pipette section 24, and a light receiving and irradiating section 26 of the measuring device provided external to the pipette section 24. In the drawing and discharging section 25 is provided a cylinder 27, and a nozzle section 28 communicated with the cylinder 27 through a pipe.

The pipette section 24 has a mounting section 29 removably mounted on the nozzle section 28 via an O-ring 30, a small diameter section 31 having a single inlet/outlet 33 at a tip end, and which is insertable into a container 19 external to the device for containing, reacting and measuring 23, and a large diameter section 32 provided between the small diameter section 31 and the mounting section 29 and having a diameter larger than that of the small diameter section 31 for containing the integrated carrier 22. The opening of the mounting section 29 constitutes a container opening for insertion and accommodation of the integrated carrier 22.

The shape and size of the large diameter section 32 is determined by the shape and size of the integrated carrier 22. The size and shape of the large diameter section 32 is a size where the integrated carrier 22 can be easily contained inside the large diameter section 32 with a margin, and is preferably a size and shape so that a gap produced between the inner wall of the large diameter section 32 and the surface of the base member 15 of the integrated carrier 22 is small to the extent that the base member 15 is easily wetted with a small amount of liquid but does not adhere to the inner wall of the large diameter section 32. Here the amount of liquid is for example approximately 100µ liters.

The drawing and discharging section 25 is for drawing and discharging the liquid 20 into and from the large diameter section 32 via the inlet/outlet 33. Furthermore, with this embodiment, while not shown in the figure, this has a moving mechanism capable of relatively moving the inlet/outlet 33 between externally provided containers 19, 34, 35 and 37.

Moreover, a light receiving and irradiating section 26 of the measuring device is one which uses for example an optical fiber for irradiating excitation light and receiving the fluorescence, being a movable device which can be scanned in the vertical direction external to the large diameter section 32 of the pipette section 24, and rotated through 360 degrees around the large diameter section 32.

In the device for containing, reacting and measuring 23 according to this embodiment, the pipette section 24 is removably mounted on the nozzle section 28. Consequently, as well as the case of replacing the pipette section with another pipette section of the same construction which is mountable on the nozzle section 28, a pipette with a magnetic force device provided on the outside to thereby exert a magnetic field so that magnetic particles are adhered to the inner wall and can thus be separated, may also be removeably mounted.

Since by so doing, the magnetic particles can be separated, it is possible to consistently perform processing for an even wider range also including for example extraction and separation of genetic material. Consequently, according to this embodiment, by using in common the same drawing and discharging section, various types of processing using magnetic particles, and various types of processing using base members can be consistently and automatically performed.

Next is a description based on FIG. 2, of a method for determining base sequences for analysis of a bonding substance being the target substance, using the device for containing, reacting and measuring 23 according to this embodiment.

In FIG. 2(c), at first in a step S1, a liquid 20 in which is previously suspended a target substance comprising a DNA fragment for which an unknown base sequence is to be determined and which has been has been labeled with fluorescence, is placed in the container 19.

Furthermore, an integrated carrier 22 with the base member 15 with various already known oligonucleotides with their base sequences and each of their fixed positions associated, wound around the core 21, is contained inside the large diameter section 32 of the pipette section 24 serving as the container section, and after this the pipette section 24 is mounted on the nozzle section 28.

In step S1, a probe solution with a predetermined reagent mixed in a liquid in which is suspended the target substance labeled with a fluorescent substance or the like, is pre-heated for a few minutes at approximately 95° C. in a constant temperature tank 34 provided with a Peltier element. Then the current direction is changed to thereby cool the solution in a condition where this is held at a normal temperature or a different temperature to normal if required, to adjust the solution to an easily hybridized form. In determining the unknown base sequence of the DNA fragment, needless to say as a pre-requisite, in addition to the hybridization process, a process for denaturation of the DNA fragment is necessary.

In step S2, the small diameter section 31 of the pipette section 24 is moved to the container 19 and inserted therein. The container 19 is held in the constant temperature tank 34 at normal temperature, or if required at a temperature different from the normal temperature, and incubation and reaction is performed over a few minutes to a few hours.

In step S3, after completion of reaction, the small diameter section 31 of the pipette section 24 is moved and inserted into the container 35 which contains a first cleaning solution 36 at room temperature, and this is then shaken and washed so that excess probe solution in which is suspended the target substance and the like is removed.

In step S4, after the first washing, the small diameter section 31 of the pipette section 24 is moved and inserted into the container 37 which contains unused second cleaning solution 38, and this is again shaken and washed, and the remaining probe solution is removed.

In step S5, the light receiving and irradiating section 26 of the measuring device measures from outside of the integrated carrier for which washing is completed, by scanning the perimeter of the large diameter section 32 vertically and through 360 degrees therearound with the scanning section.

Figure 3:
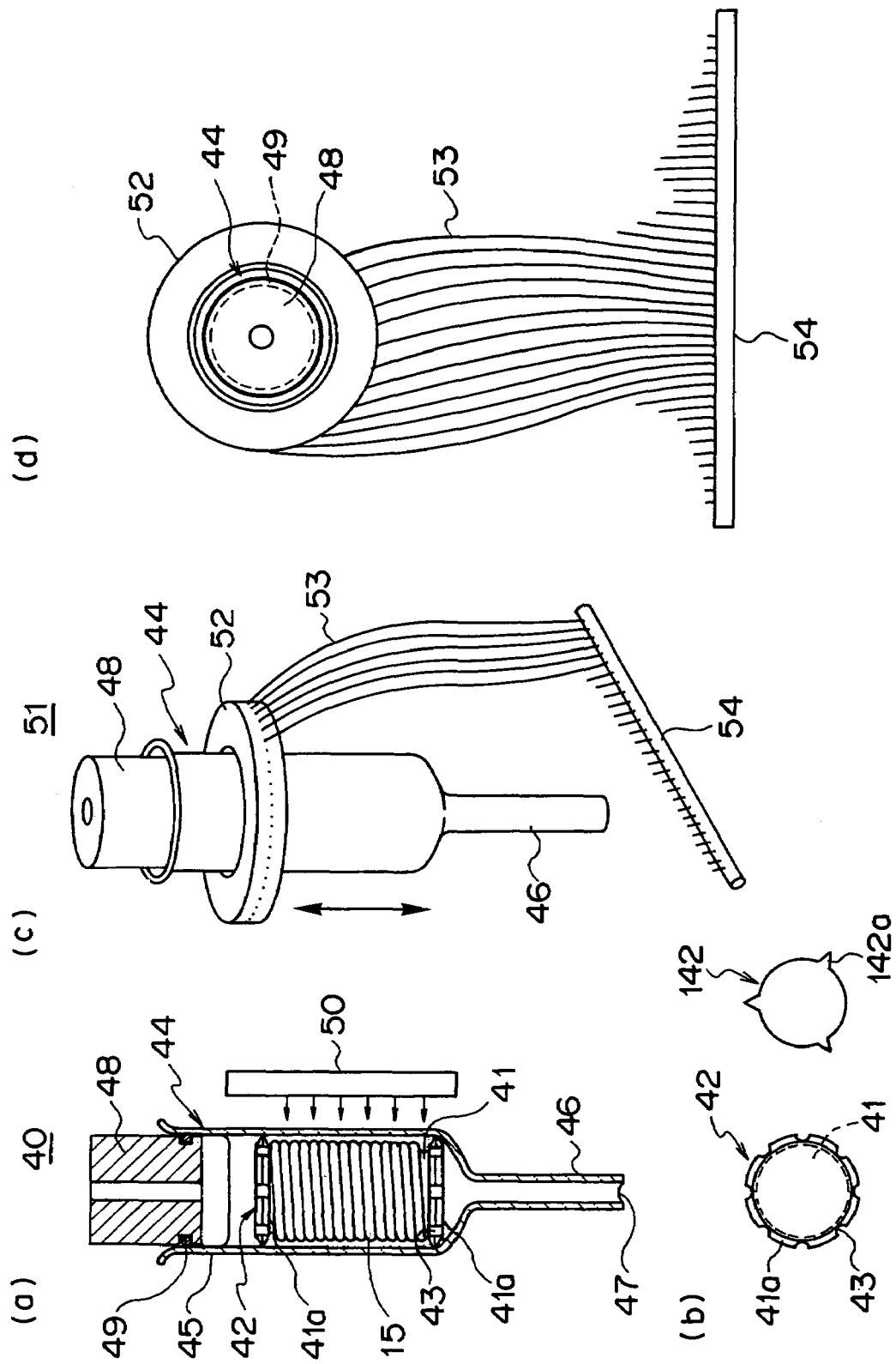
FIG. 3 is a schematic diagram of a device for containing, reacting and measuring according to a third and fourth embodiment of the present invention.

Next, is a description of a device for containing, reacting and measuring 40 according to a third embodiment, based on FIG. 3.

FIG. 3(a) shows the device for containing, reacting and measuring 40 according to the third embodiment. This device for containing, reacting and measuring 40 uses another integrated carrier 42. The integrated carrier 42, as shown in FIG. 3(a) has the base member 15 wound around a core 41 as the carrier.

As shown in FIG. 3(b), at opposite rims of the core 41 are respectively provided annular protruding portions 41a serving as the protective portions. By means of these protective portions, the base member 15 is bound so as not to come off from the core 41 being the carrier, and contact between an inner wall of a pipette section 44 serving as a later mentioned container section and the base member 15 is prevented, so that the liquid passing the surface of the base member 15 flows smoothly, and the integrated carrier 42 is positioned inside the container section, thus enabling reliable measurement. Consequently, the core 41 is formed in an overall spool shape.

On these annular protruding portions 41a are provided a plurality of cut out portions 43 so that the liquid can pass therethrough, and the contact portions at the tip of the annular protruding portion 41a which contact with the inner wall are formed in a wedge shape so that the contact area with the inner wall is minimal. As a result, liquid residue is prevented, and the process can be smoothly performed. The height of the annular protruding portions 41a is made a height exceeding the thickness of the wound base member 15, to thereby prevent the base member 15 from touching or adhering to the inner wall.

Furthermore, instead of the annular protruding portions 41a, protective portions 142 as shown in FIG. 3(b) may be provided. With these protective portions 142, a plurality of radially protruding portions 142a are provided, and the height of these protruding portions 142a is set so as to exceed the thickness of the base member 15.

The device for containing, reacting and measuring 40 which uses the integrated carrier 42, has a pipette section 44 serving as the container section, a drawing and discharging section 48 for performing drawing and discharging into and from the pipette section 44, and a linear light receiving and irradiating section 50 provided external to the pipette section 44. Reference symbol 48 denotes a nozzle section provided in the drawing and discharging section 48.

The linear light receiving and irradiating section 50 is attached to a rod shape support member with tip sections of a large number of optical fibers arranged in a line. Each of the fibers is connected to a photodetector and a light source for irradiating excitation light for exciting the fluorescent substances used in the labeling. As a result, the fluorescence excited thereby can be simultaneously received.

Furthermore, the linear light receiving and irradiating section 50 may be such that direct photodetectors are arranged in a line, and there is provided a light source for irradiating excitation light. This linear light receiving and irradiating section 50 is provided so as to be able to be turned through 360 degrees around the periphery of the large diameter section 45 by means of a scanning section (not shown in the figure). Furthermore, the mounting portion containing the pipette section 44 may be provided so as to be able to be rotated through 360 degrees around the axis of the pipette section 44.

This linear light receiving and irradiating section 50 corresponds to the measuring device.

The pipette section 44 has a removably mounted large diameter section 45 engaged with the nozzle section 48 via an O-ring 49, and which contains the integrated carrier 42, and a small diameter section 46 with a tip having an inlet/outlet 47, which can be inserted into a container external to the device for containing, reacting and measuring 40. Here the diameter of the large diameter section 45 is for example an inner diameter of approximately 4 mm. The opening of the large diameter section 45 constitutes the container opening for insertion and accommodation of the integrated carrier.

Here the annular protruding portion 41a of the integrated carrier 42 is preferably formed in a size to contact with the inner wall of the large diameter section 45. The outside diameter of the integrated carrier 42 is for example approximately 3.8 mm.

FIG. 3(c) shows a device for containing, reacting and measuring 51 according to a fourth embodiment. This device for containing, reacting and measuring 51 uses an annular light receiving and irradiating section 52 as the measuring device, instead of the linear light receiving and irradiating section 50 formed in the linear shape. To the annular light receiving and irradiating section 52 is fitted an annular support member with tip portions of a large number of optical fibers 53 arranged annularly. These optical fibers 53 irradiate excitation light and at the same time receive fluorescence.

The other ends of the optical fibers 53 are connected to a line sensor 54 comprising photodetectors arranged in a line. Furthermore, the other ends of the optical fibers 53 may be connected to a planar CCD element. Moreover, this annular light receiving and irradiating section 52 is provided so as to be moveable vertically by means of a scanning section (not shown in the figure). Moreover, an equipment part including the pipette section 44 may be provided so as to be moveable vertically by means of the scanning section.

Figure 4:
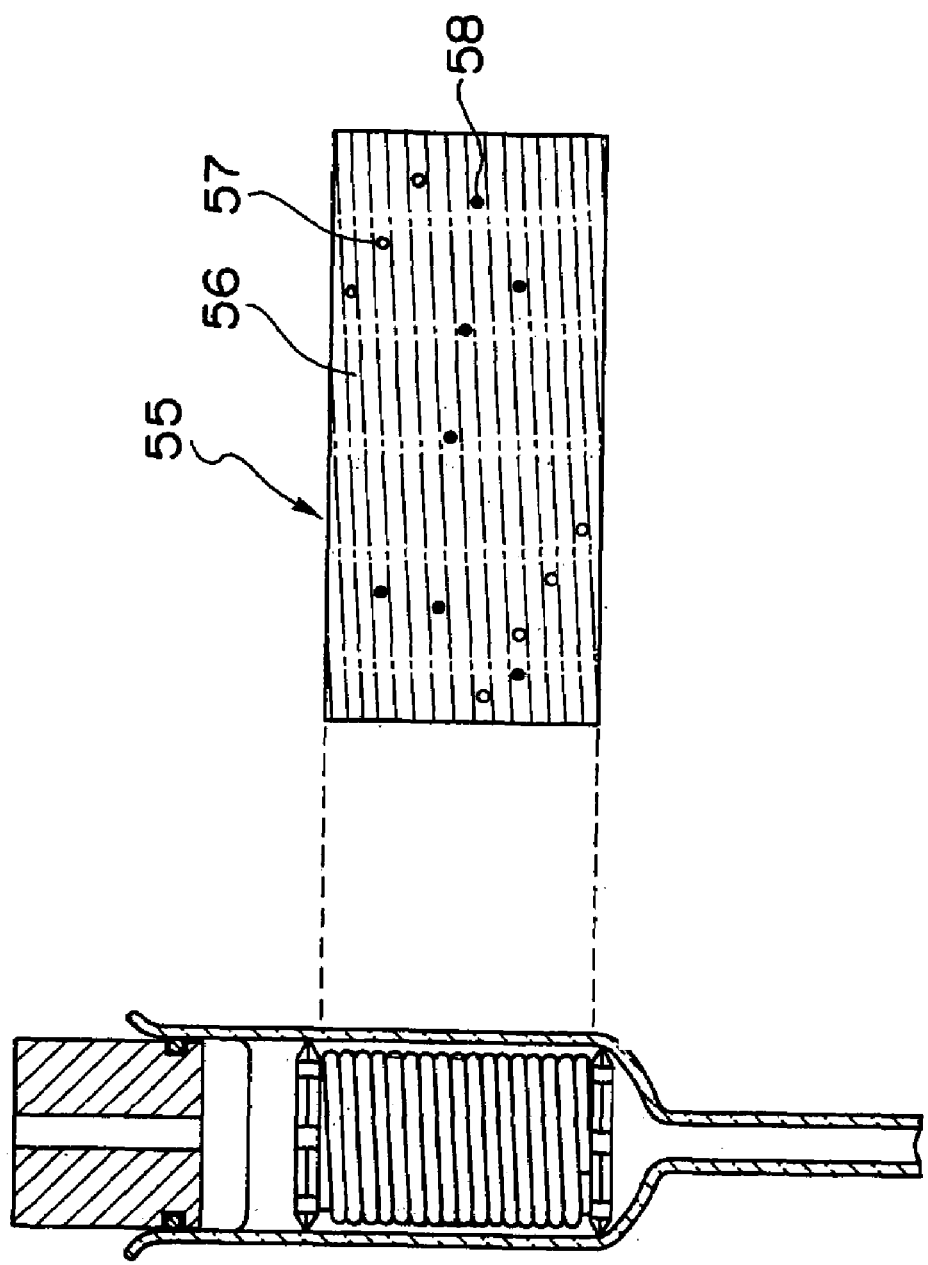
FIG. 4 is a diagram showing an example of an identification pattern of a device for containing, reacting and measuring according to the third and fourth embodiments of the present invention.

FIG. 4 shows one example of a measured identification pattern 55 with fixed positions, and qualitative and quantitative information for the fixed positions displayed as a plain surface. Here reference symbol 56 denotes positions on an image of the base member 15. Reference symbol 57 denotes reference points which are labeled beforehand so as to become references for specifying fixed positions of the base member 15. Reference symbol 58 shows fixed positions where the labeled target substance has been bonded. According to this example, the measurement results for each of the labeled fixed positions may be processed as planar information.

Figure 5:
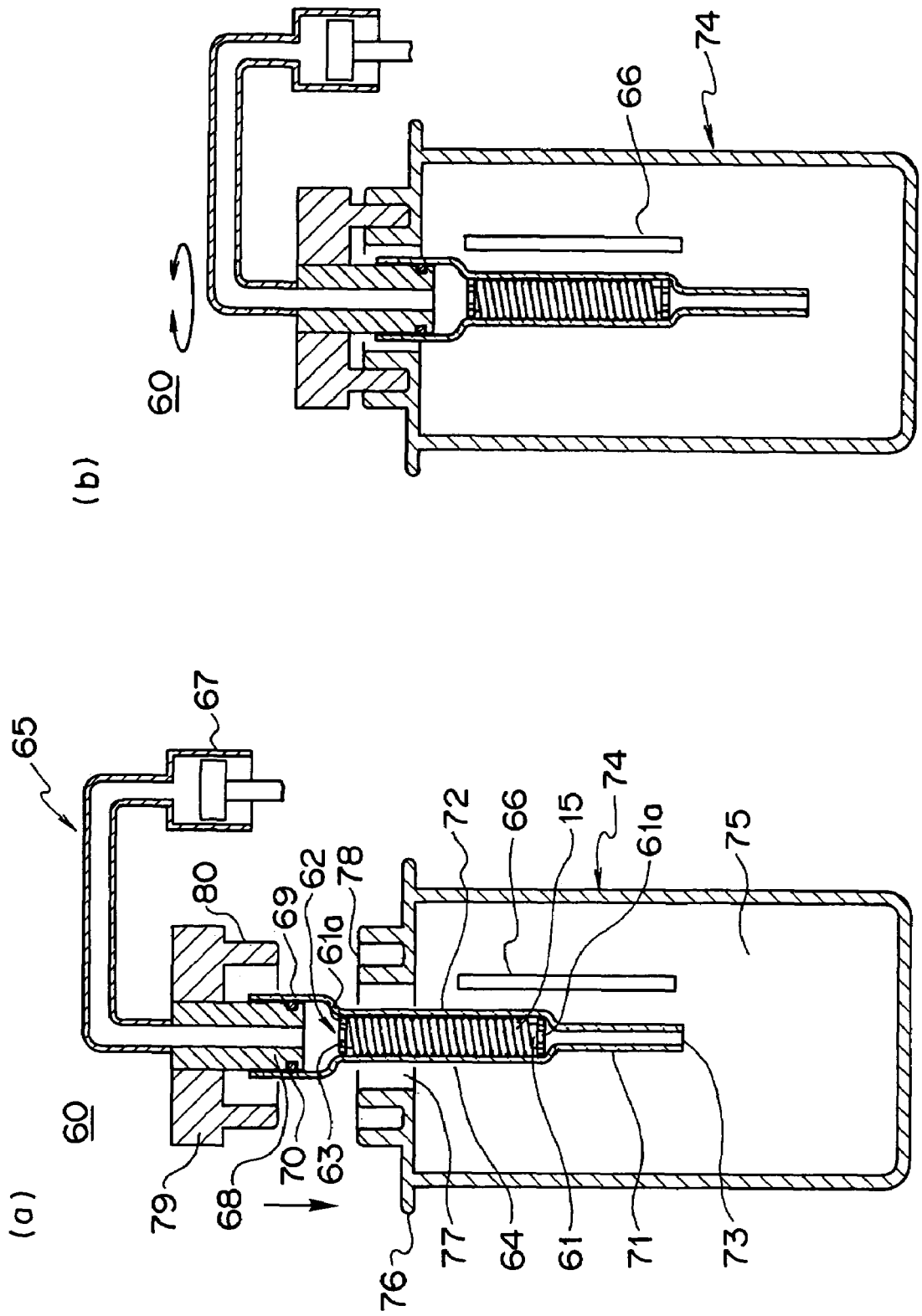
FIG. 5 is a schematic diagram of a device for containing, reacting and measuring according to a fifth embodiment of the present invention.

Next is a description of a device for containing, reacting and measuring 60 according to a fifth embodiment, based on FIG. 5. As shown in FIGS. 5(a) and (b), the device for containing, reacting and measuring 60 according to this embodiment has; a pipette section 64 serving as the container section, a drawing and discharging section 65 for drawing and discharging into and from the pipette section 64, and a light receiving and irradiating section 66 provided external to the pipette section 64. In the drawing and discharging section 65 is provided a cylinder 67, and a nozzle section 68 communicated with the cylinder 67 through a pipe.

The pipette section 64 has a removably mounted mounting section 69 engaged with the nozzle section 68 via an O-ring 70, a small diameter section 71 with a tip having an inlet/outlet 73, and which is insertable into a container external to the device for containing, reacting and measuring 60, and a large diameter section 72 provided between the small diameter section 71 and the mounting section 69 and having a diameter larger than that of the small diameter section 71 for containing an integrated carrier 62.

The integrated carrier 62 is one where the base member 15 is wound around a core 61. At opposite ends of the core 61 are respectively provided annular protruding portions 61a serving as the protective portions for protecting so that the base member 15 does not come off from the core 61 and the base member 15 does not contact with the inner wall, and for ensuring smooth flow of the liquid, and for positioning. The core 61 is formed overall in a spool shape, and on these annular protruding portions 61a are provided a plurality of cut out portions 43 so that the liquid can pass therethrough.

Here the annular protruding portions 61a of the integrated carrier 62 are preferably formed in a size so as to contact with the inner wall of the large diameter section 72.

The drawing and discharging section 65 is for drawing and discharging the liquid into and from the large diameter section 72 via the inlet/outlet 73. Furthermore this embodiment, while not shown in the figure, has a moving mechanism which can relatively move the inlet/outlet 73 between various processing areas and processing positions such as externally provided containers, and a later described light shielding box 74.

With this embodiment, the light receiving and irradiating section 66 of the measuring device is provided in the light shielding box 74. The light shielding box 74 is used for shutting off noise of excess light generated from the exterior or from the interior at the time of measuring the fluorescence generated by the integrated carrier 62. The light shielding box 74 has a box body 75 provided with the light receiving and irradiating section 66 of the measuring device and with the pipette section 64 inserted thereinside, and a cover 76 provided on an opening of the box body 75. An aperture 77 is formed in a central portion of the cover 76 for enabling insertion of the pipette section 64. Moreover, around the periphery of the aperture 77 a double annular wall section 78 is provided upwardly protruding so as to form an annular groove therebetween.

On the other hand, an annular cover plate 79 for covering the aperture 77 is provided so as to protrude sideways from the surroundings of the upper portion of the nozzle section 68. On a lower side of the cover plate 79 provided so as to protrude downwards, is an annular protrusion 80 for insertion into the groove formed by the double annular wall 78 to form an enclosed space thereinside. Here the cover plate 79, the double annular wall 78 and the annular protrusion 80 correspond to a closure device.

Furthermore, with the device for containing, reacting and measuring 60 according to this embodiment, there is provided a rotation section (not shown in the figure) serving as the scanning section, which can scan the whole periphery of a part containing the pipette section 64, in relation to the central axis of the pipette section 64. By rotation by this rotation section, the annular protrusion 80 slides inside the groove formed in the double annular wall section 78. As a result, complete light shielding is achieved, and all of the fixed positions provided on the integrated carrier 62 contained inside the large diameter section 72 can be scanned and the light received without any leakage.

FIG. 5(a) shows the condition where the pipette section 64 is being moved downward by the moving section (not shown in the figure) in order to insert the pipette section 64 inside the light shielding box 74, while FIG. 5(b) shows the condition where insertion of the pipette section 64 into the light shielding box 74 has been completed, and measurement is being performed.

The measuring device parts other than the light receiving and irradiating section 66 may be provided inside the light shielding box 74 or outside. In the case of the latter, the light shielding box 74 can be made smaller.

Figure 6:
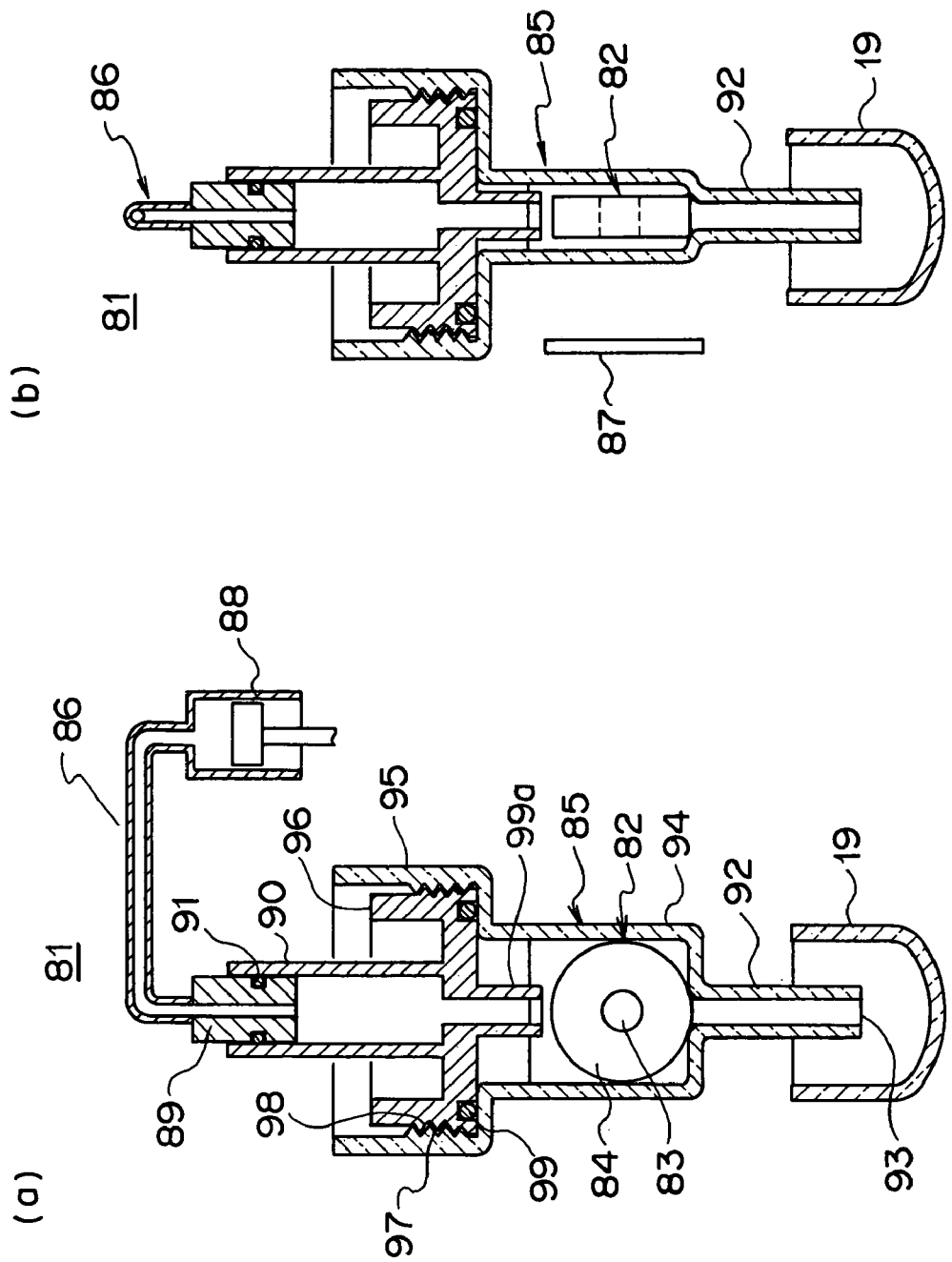
FIG. 6 is a schematic diagram of a device for containing, reacting and measuring according to a sixth embodiment of the present invention.

Next is a description of a device for containing, reacting and measuring 81 according to a sixth embodiment, based on FIG. 6.

The device for containing, reacting and measuring 81 according to this embodiment, as shown in FIG. 6(a) and (b) has; a pipette section 85 serving as the container section, a drawing and discharging section 86 for drawing and discharging into and from the pipette section 85, and a light receiving and irradiating section 87 provided external to the pipette section 85. In the drawing and discharging section 86 is provided a cylinder 88, and a nozzle section 89 communicated with the cylinder 88 through a pipe.

The pipette section 85 has a removably mounted mounting section 90 engaged with the nozzle section 89 via an O-ring 91, a small diameter section 92 with a tip having an inlet/outlet 93, and which is insertable in a container 19 external to the device for containing, reacting and measuring 81, and a large diameter section 94 provided between the small diameter section 92 and the mounting section 90 and having a diameter larger than that of the small diameter section 92 for containing an integrated carrier 82. The opening of the large diameter section 94 constitutes the container opening for insertion and accommodation of the integrated carrier.

The integrated carrier 82 has a region 84 where this is wound as a spiral within a plane on the core 83 being the center of the base member 15, and is different from the aforementioned integrated carriers 42 and 62 where the base member 15 is wound in one layer only in a cylindrical shape.

Furthermore, in the device for containing, reacting and measuring 81 according to this embodiment, a cylindrical external screw section 96 is provided beneath the mounting section 90 with a thread 98 provided on an external surface thereof. On the other hand, a cylindrical recess screw section 95 is provided on an upper portion of the large diameter section 94, with a screw thread 97 provided on an internal surface thereof. Moreover, an O-ring 99 is provided between the external screw section 96 and the recess screw section 95 to give high water tightness.

As a result, with this embodiment, the integrated carrier 82 which has a greater diameter than the mounting section 90 can be easily accommodated by unfastening the external screw section 96 from the recess screw section 95. A pipe 100 of a predetermined length may be provided so as to protrude from the lower side of the external screw section 96 to prevent lifting of the integrated carrier 82, and enable the integrated carrier 82 to be accommodated and fixed in a predetermined position.

Furthermore, instead of the case where, as described above, the large diameter section and the mounting section are provided so as to be able to be opened and closed by means of the screw sections so that the base member (or the DNA chip or the integrated carrier) is provided so as to be able to be accommodated or taken out, after accommodating the base member in the large diameter section, this may be sealed in by welding with ultrasonic welding or the like between the mounting section and the large diameter section. In this case, since from the start the base member is accommodated inside the container section, then the reliable prevention of cross-contamination is possible.

Figure 7:
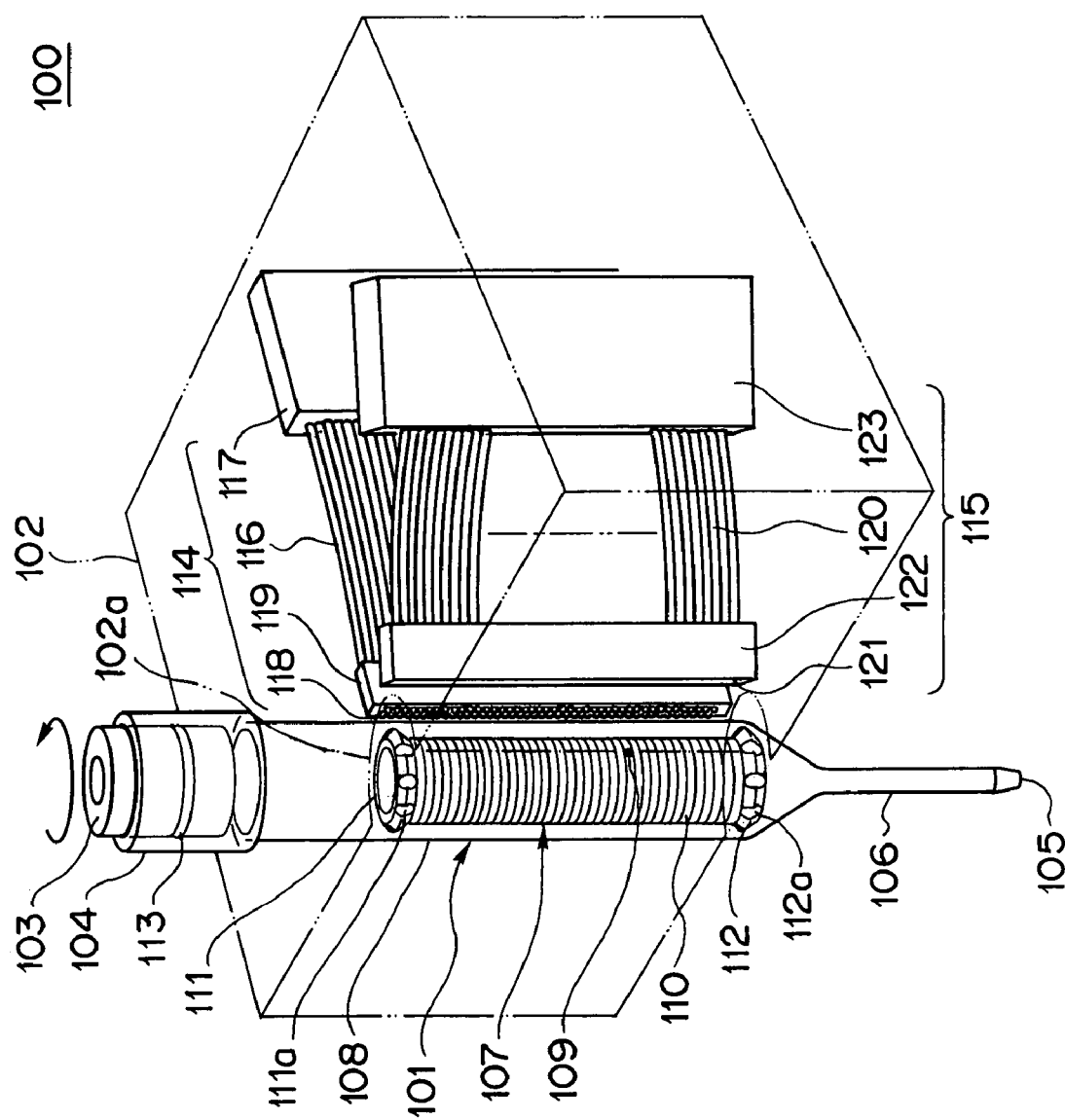
FIG. 7 is a schematic perspective view of a device for containing, reacting and measuring according to a seventh embodiment of the present invention.

FIG. 7 shows a containing, reacting and measuring device 100 according to a seventh embodiment.

The containing, reacting and measuring device 100 according to this embodiment has; a pipette section 101 serving as the container section, a drawing and discharging section for performing drawing and discharging with respect to the pipette section 101, and a measuring device provided on the outside of the pipette section 101 capable of receiving light from the pipette section 101 in a condition associated with the light emission position.

The pipette section 101 has a mounting section 104 removably mounted on the nozzle section 103 of the drawing and discharging section via an O-ring, a small diameter section 106 having a single inlet/outlet 105 at a tip end, and which is insertable into a container external to the device for containing, reacting and measuring 100, and a transparent large diameter section 108 capable of containing the integrated carrier 107, provided between the small diameter section 106 and the mounting section 104 and having a diameter larger than that of the small diameter section 106.

The opening of the mounting section 104 constitutes a container opening for inserting and containing the integrated carrier 107 in the large diameter section 108.

The shape and size of the large diameter section 108 is determined by the shape and size of the integrated carrier 107. The size and shape of the large diameter section 108 is a size where the integrated carrier 107 can be easily contained inside the large diameter section 108 with a margin, and is preferably a size and shape so that a gap produced between the inner wall of the large diameter section 108 and the surface of the integrated carrier 107 is small to the extent that the integrated carrier 107 is easily wetted with a small amount of liquid but the surface thereof does not adhere to the inner wall of the large diameter section 108. Here the amount of liquid is for example approximately 100μ liters.

The drawing and discharging section is for drawing and discharging the liquid into and from the large diameter section 108 via the inlet/outlet 105. Furthermore, with this embodiment, while not shown in the figure, this has a moving mechanism capable of relatively moving the inlet/outlet 105 between externally provided containers.

Moreover, the integrated carrier 107 contained inside the pipette section 101 is one where a base member 110 on which various kinds of substances for detection 109 are fixed at respective fixed positions arranged in a spaced apart condition, is wound on a cylindrical core (not shown in the figure). The integrated carrier 107 has annular protruding portions 111 and 112 on the upper end and lower end of the carrier, which have a plurality of cutout portions 111a and 112a, and which have a shape to fit tightly against the inner wall of the large diameter section 108, and is fixed inside the large diameter section 108 by means of these. The cutout portions 111a and 112a are for allowing liquid to pass in the vertical direction. As a result, the integrated carrier 107 is fixed and contained inside the large diameter section 108 in a condition immersed in the liquid.

Reference symbol 113 denotes an O-ring provided between the nozzle section 103 and the mounting section 104 for maintaining water tightness.

The integrated carrier 107 is one where various kinds of substances for detection 109, for example oligonucleotides having already known various base sequences, are arranged and fixed in a spaced apart condition, and has a base member 110 formed in a long and slender shape such as a filament, a braid, or tape with various substances for detection 109 and their fixed positions associated, and a core being a carrier on which the base member 110 is wound. The substances for detection 109 are ones which show that, by bonding with a bonding substance being a labeled target substance, their fixed position are identified. By analyzing these labeled fixed positions, the unknown chemical structure of the target substance can be determined.

The drawing and discharging section has, in addition to the nozzle section 103, a pump or the like (not shown in the figure) which communicates with the nozzle section 103.

The measuring device has a measuring device body 102 having an irradiating section 114 for irradiating an excitation light beam for exciting the fluorescent substance, and a light receiving section 115 for receiving fluorescent light excited by the irradiation, and a scanning section (not shown in the figure) for rotationally driving the nozzle section 103 to scan the integrated carrier 107.

The irradiating section 114 has an optical fiber bundle 116 having a large number of optical fibers, a light source 117 for generating a trigger beam, and an optical fiber support section 119 which supports the optical fiber tip portions 118 arranged close to the outer face of the large diameter section 108, in column form along the axial direction of the nozzle section 103 and hence the pipette section 101. The layout of the tip portions of the optical fibers, is for example an array in matrix form of ten columns by 300 rows. Furthermore, the tip portions of the optical fibers may be given a lens function.

The light receiving section 115 has an optical fiber bundle 120 having a large number of optical fibers, an optical fiber support section 122 which supports the tip portions 121 of the optical fibers arranged close to the outer face of the large diameter section 108, in column form along the axial direction of the nozzle section 103 and hence the pipette section 101, and a light receiving device 123 comprising a line shape optical sensor or CCD camera provided on the other end side of the optical fiber bundle 121.

Figure 8:
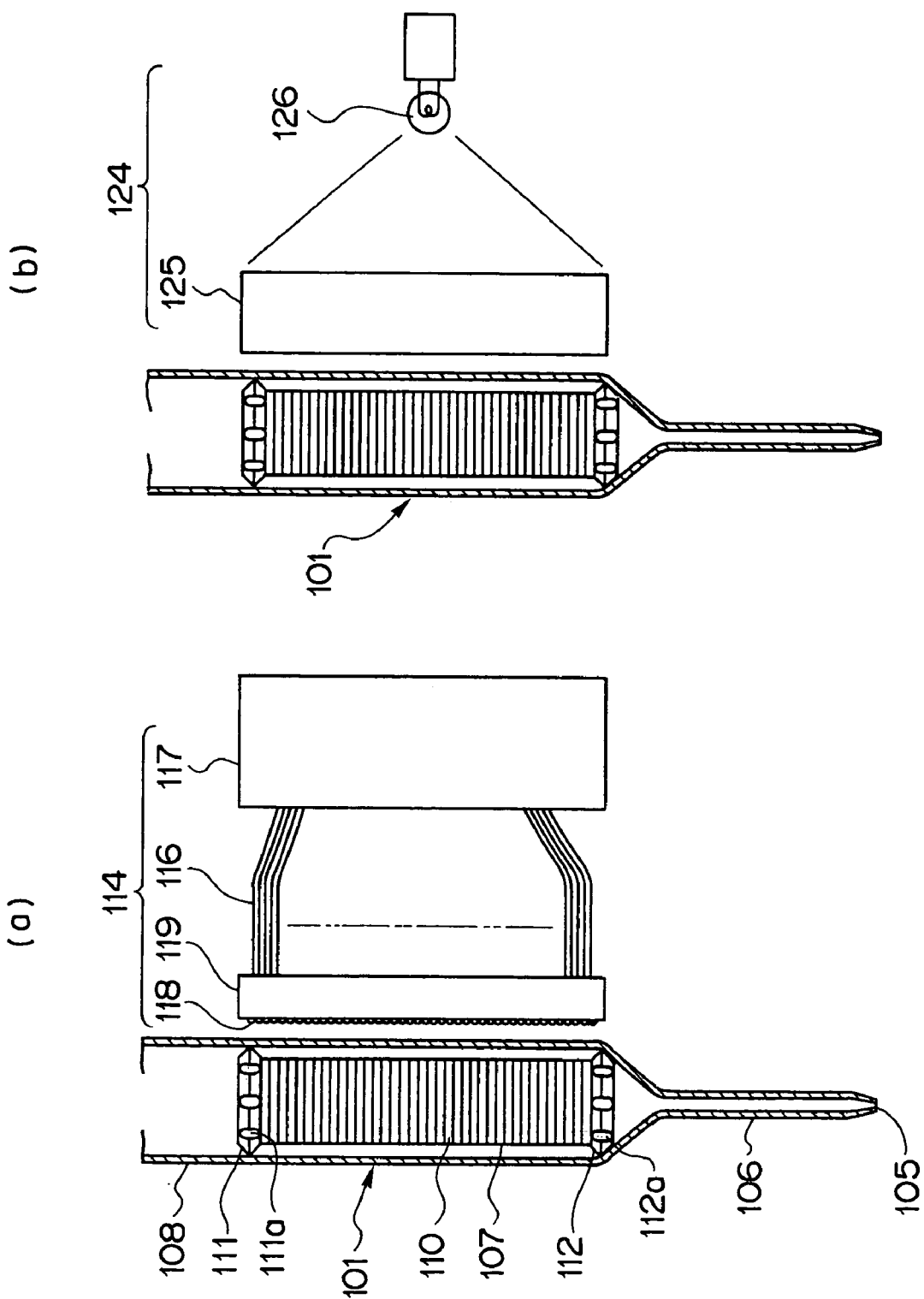
FIG. 8 shows a pipette section and an illumination section related to the seventh embodiment of the present invention.

FIG. 8(*a*) shows in detail the positional relationship between the pipette section 101 and the measuring device body 102 shown in FIG. 7. As shown in this figure, the tip portion 118 of the optical fiber bundle 116 is arranged across the whole of the integrated carrier 107 contained in the large diameter section 108. Furthermore, FIG. 8(*b*) shows an irradiating section 124 according to another example. The irradiating section 124, instead of using the optical fiber bundle uses fiberglass 125. By illuminating the rear side face of the fiber glass 125 with a light source 126, a uniform light can be shone onto the integrated carrier 107 contained in the large diameter section 108.

Figure 9:
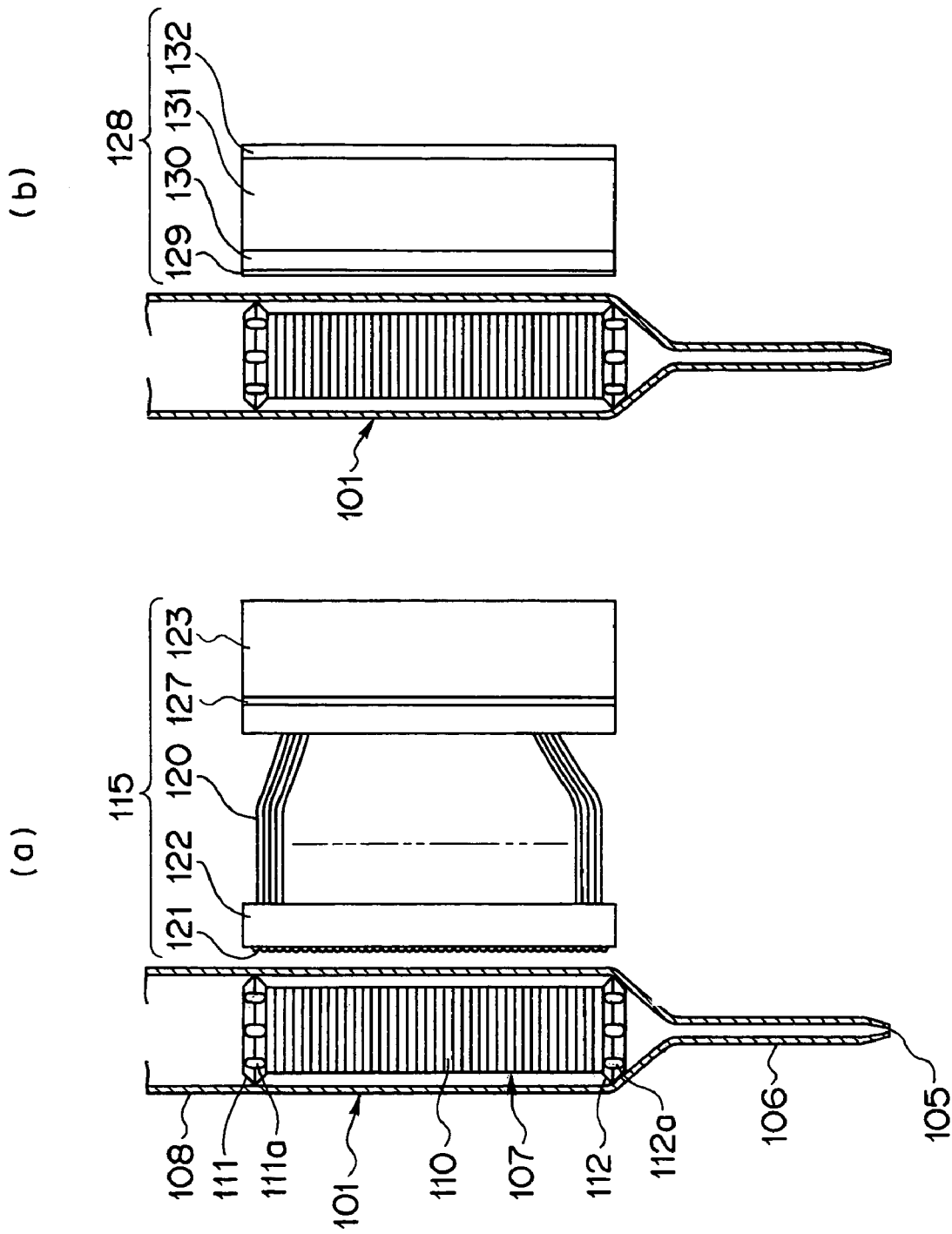
FIG. 9 shows a pipette section and a light receiving section related to the seventh embodiment of the present invention.

FIG. 9(*a*) shows in detail the positional relationship between the pipette section 101 and the light receiving section 115 shown in FIG. 7. As shown in this figure, the tip portion 121 of the optical fiber bundle 120, is arranged across the whole length of the integrated carrier 107 contained in the large diameter section 108. Here, reference symbol 127 denotes a line sensor for sensing light. Instead of providing the line sensor 127, a CCD camera may be provided.

FIG. 9(*b*) shows a light receiving section 128 according to another example. The light receiving section 128 comprises a vapor deposition layer 129 as a filter, a fixed glass layer 130 for performing adjustment of the focus, fiber glass 131, and a CCD camera or line sensor 132.

Figure 10:
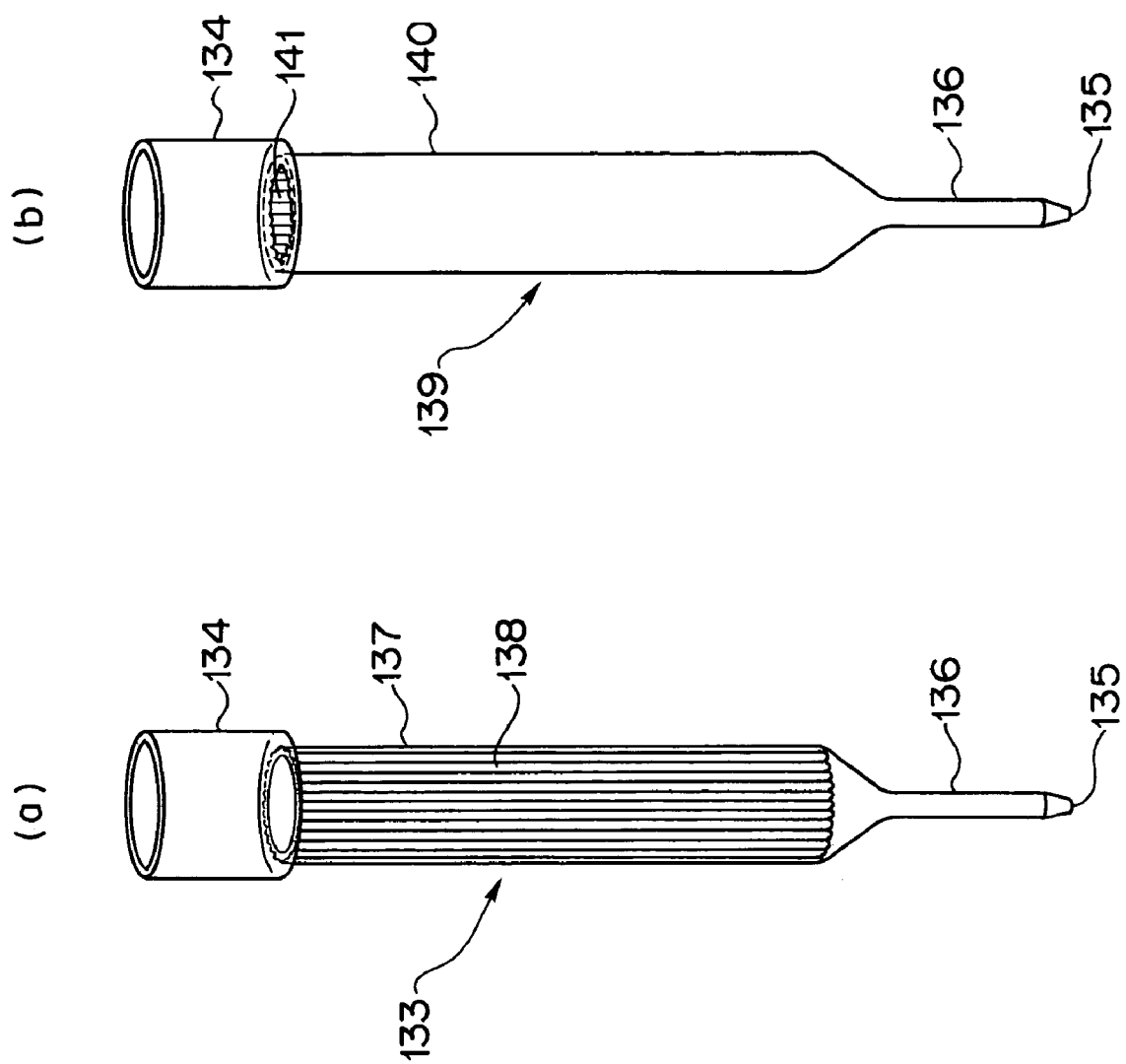
FIG. 10 shows a pipette section related to an eighth embodiment of the present invention.

FIG. 10 shows a pipette section according to an eighth embodiment.

The pipette section 133 shown in FIG. 10(*a*), as with the aforementioned pipette section 101, has a mounting section 134 which is removably mounted on the nozzle section via an O-ring, a small diameter portion 136 having one inlet/outlet 135 on the tip end, and capable of insertion into a container outside of the containing, reacting and measuring device, and a transparent large diameter section 137 provided between the small diameter section 136 and the mounting section 134, having a diameter which is larger than that of the small diameter section 136, and capable of containing the integrated carrier. On the outside face of the large diameter section 137 there is provided a plurality of cylindrical lenses 138 having generatrix parallel with the axial direction. The cylindrical lenses 138 do not have a refractive effect in a plane containing the generatrix, but have a similar refractive effect to a normal lens in a plane perpendicular to the generatrix.

FIG. 10(*b*) shows another example of a pipette section 139 according to the eighth embodiment. The pipette section 139, excluding the large diameter section 140 is the same as the pipette section 133. In the large diameter section 140 on the inside face thereof is provided a large number of cylindrical lenses 141 having generatrix parallel with the axial direction. The cylindrical lenses 141 do not have a refractive effect in a plane containing the generatrix, but have a similar refractive effect to a normal lens in a plane perpendicular to the generatrix.

Figure 11:
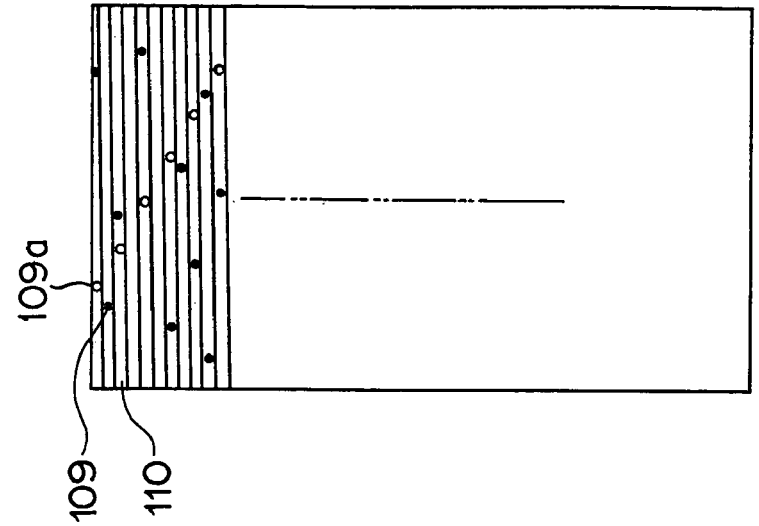
FIG. 11 shows positional relationship between the pipette section and the illumination section and light receiving section in relation to the eighth embodiment of the present invention.
Figure 11:
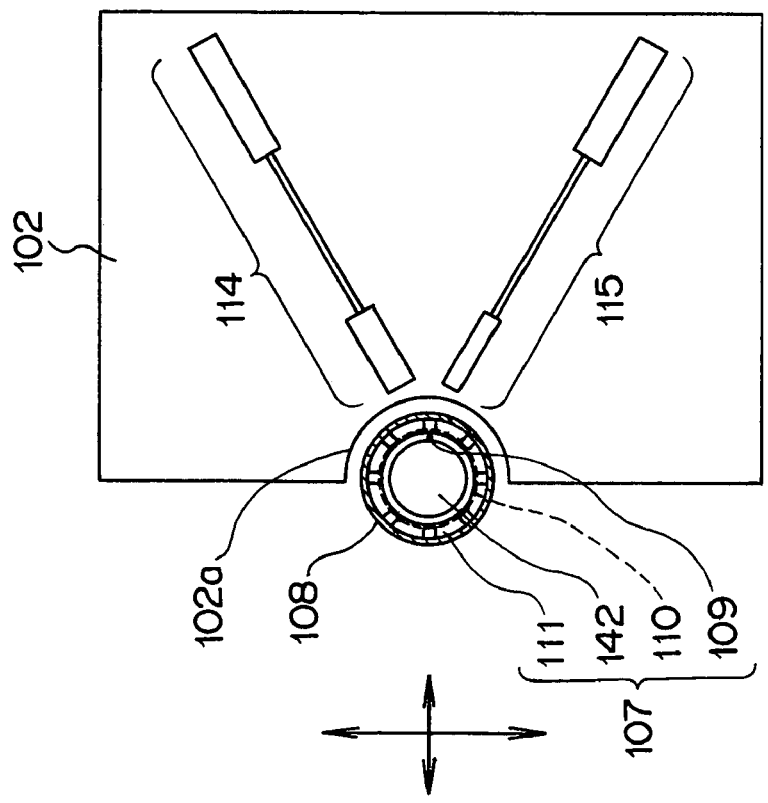

FIG. 11 shows the positional relationship between the pipette section 101 of the containing, reacting and measuring device 100 and the irradiating section 114 and light receiving section 115 of the measuring device body 102. Here, reference symbol 142 denotes a core of the integrated carrier 107. The pipette section 101 is capable of translational movement along the X-axis, Y-axis and Z-axis directions with respect to the measuring device body 102, and when carrying out measurement, by translationally moving this in a semicircular shape groove section 102*a* of the measuring device body 102 arranged with the tip portions of the irradiating section 114 and the light receiving section 115, these are positioned at the side face of the integrated carrier 107 contained in the large diameter section 108. Then, by rotating the nozzle section 103, the fixed positions and qualitative and quantitative information of the fixed positions can be obtained. If these measurement results are displayed on a plain surface, then for example this gives the image 143 as shown in FIG. 11(*b*). Such an image 143 may be displayed on a display section as an output section connected to the measuring device body 102 (not shown in the figure) or printed out or stored in a storage section. By measuring the light emission position being the image 143, then structure and the like of the target substance can be analyzed. Here, reference symbol 109*a* denotes marks due for example to a light emission substance, used for identifying the fixed position. This mark is set so as to also represent the standard strength of the quantitative information.

Figure 12:
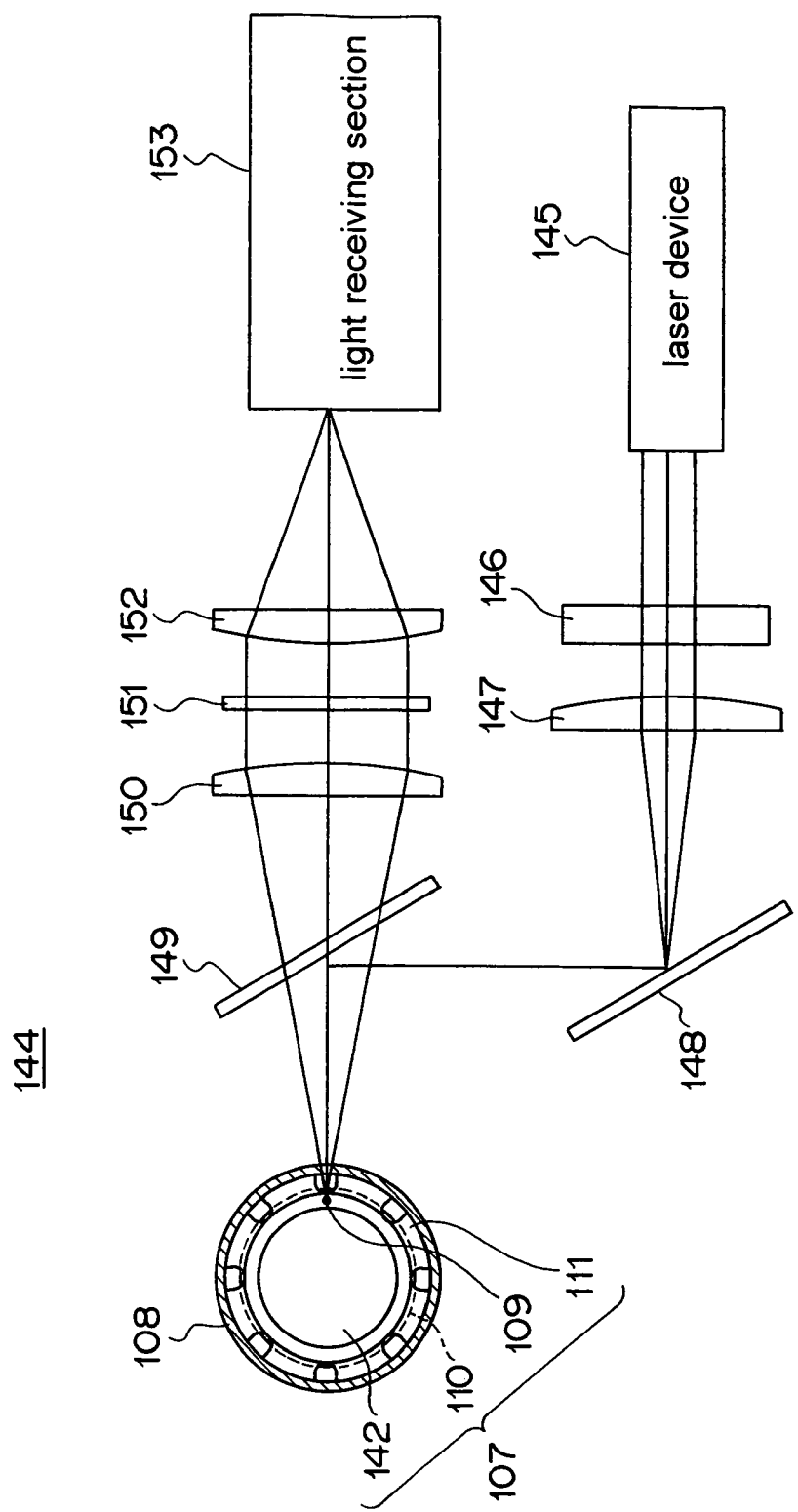
FIG. 12 shows a device for containing, reacting and measuring according to a ninth embodiment of the present invention.

Next is a description of a containing, reacting and measuring device 144 according to a ninth embodiment based on FIG. 12. The containing, reacting and measuring device 144, as shown in the figure, has as the illumination section, a laser device 145 serving as an illumination section which outputs a planner sheet of light aligned along the longitudinal direction (the direction perpendicular to the paper in FIG. 12) along an axial direction of the large diameter section 108 of the pipette section 101, and the laser beam irradiated from the laser device 145 passes through a filter 146 for removing wavelengths other than of the necessary excitation light for exciting the fluorescent substance. Then, by means of a semicylinder type cylindrical lens 147, this is converged in a planar direction (transverse direction) parallel to the paper, and by means of half mirrors 148 and 149, a laser beam having a predetermined length in the vertical direction is irradiated onto the integrated carrier 107 contained inside the large diameter section 108. The light in a line shape containing fluorescence and having a predetermined length in the longitudinal direction which is generated by the irradiated laser light, passes through the half mirror 149 and by means of a cylindrical lens 150, is made parallel light, and passes through a filter 151, and is then converged in the transverse direction by a cylindrical lens 152, and is received by a light receiving section 153.

Next is a detailed description of a device for containing, reacting and measuring 155 having a pipette section being a multi set (in this example six sets) container section, according to a tenth embodiment, based on FIGS. 13, 14, 15 and 16.

Figure 13:
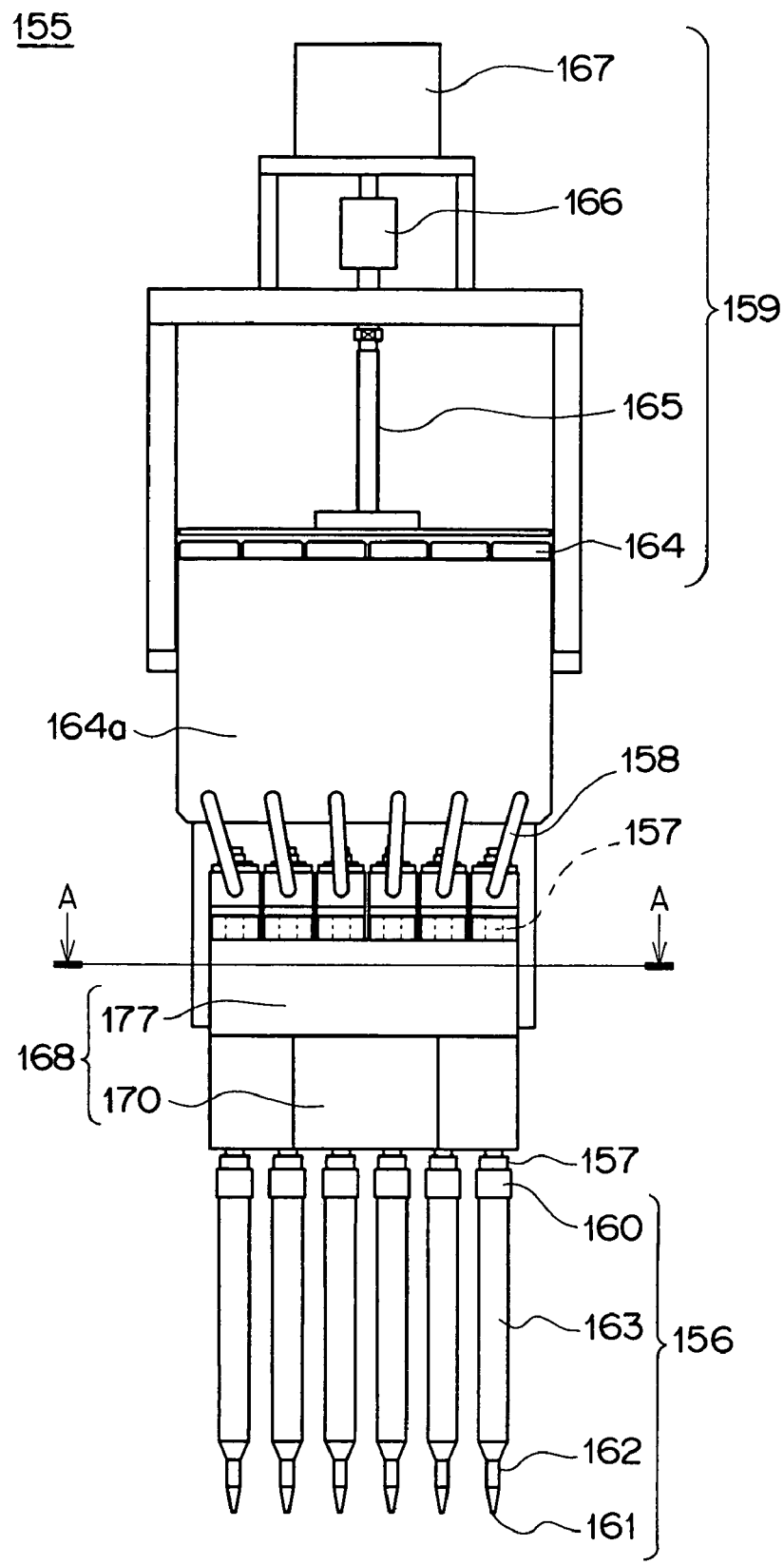
FIG. 13 is a front view showing a device for containing, reacting and measuring according to a tenth embodiment of the present invention.

As shown from the front face in FIG. 13, the device for containing, reacting and measuring 155 according to this embodiment has; six sets of pipette sections 156, six sets of rotatably provided nozzle sections 157 on which the pipette sections 156 are mounted, and a drawing and discharging section 159 which performs drawing and discharging of a liquid with respect to the six sets of pipette sections 156, by adjusting the pressure thereof with respect to the six sets of pipette sections 156, via six sets of circular tubes 156.

The pipette section 156 has a mounting section 160 removably mounted on the nozzle section 157, a small diameter section 162 having a single inlet/outlet 161 at a tip end, and which is insertable into a container (not shown) external to the device for containing, reacting and measuring 155, and a large diameter section 164 provided between the small diameter section 162 and the mounting section 160 and having a diameter larger than that of the small diameter section 162.

Furthermore, the drawing and discharging section 159 has a cylinder block 164*a* having six sets of cylinders which are communicated with the six sets of nozzle sections 157 via the six sets of circular tubes 158, a ball screw 165 connected to cylinder rods (pistons) 164 inside the cylinder block 164*a*, which slides the six sets of cylinder rods 164 altogether in the vertical direction, and a motor 167 for rotationally driving the ball screw 165 via a coupler 166. Here reference symbol 168 denotes a section corresponding to the scanning section of the measuring device which contains the rotation mechanism which rotates the nozzle section 157.

Figure 14:
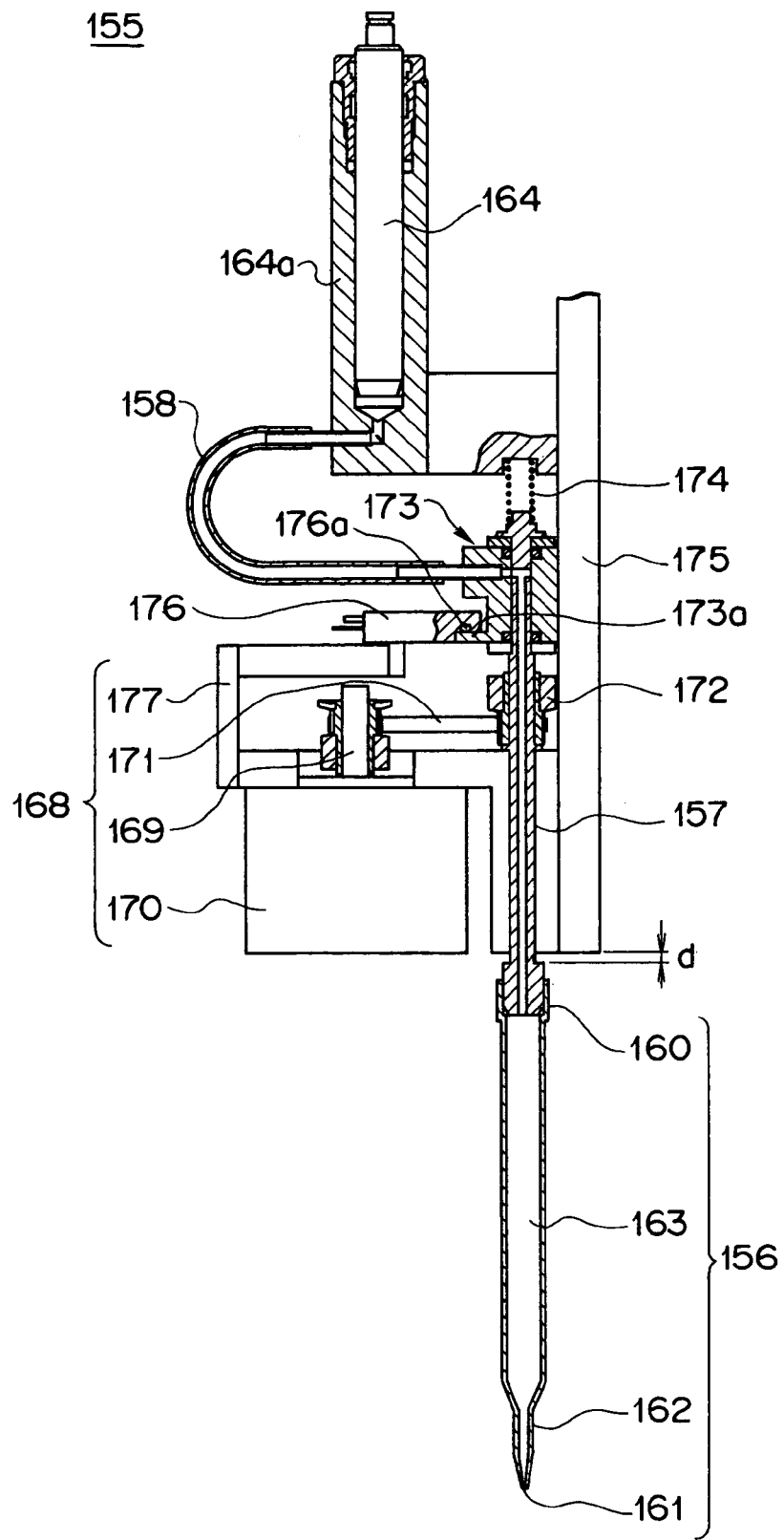
FIG. 14 is a sectional side view showing the device for containing, reacting and measuring according to the tenth embodiment of the present invention.

FIG. 14 shows a sectional view from the side of the device for containing, reacting and measuring 155 shown in FIG. 13. In the scanning section 168, a belt 171 with teeth on one side for transmitting rotation from a toothed pulley 169 provided on a rotation shaft of a later mentioned motor 178 contained in a motor containing section 170, to the nozzle section 157, is spanned between the toothed pulley 169 and a toothed pulley 172 provided on the nozzle section 157. The whole of the nozzle section 157 can be rotated by the rotation mechanism, and is supported on a frame 175 so as to be moveable by a predetermined distance d in the vertical direction. However, this is always urged downwards by means of a spring member 174 provided between an upper end 173 of the nozzle section 157 and the frame 175. Reference symbol 176 denotes an optical sensor. When the inlet/outlet 161 on the tip end of the pipette section 156 mounted on the nozzle section 157 receives a force due to contact with an external object, the whole of the nozzle section 157 is moved upwards, and a shielding section 173*a* provided on the top end section 173 thereof blocks off a photodetector 176*a* of the optical sensor 176, so that the grounding of the tip end of the pipette sections 156 can be detected. Here, reference symbol 177 denotes a rotation mechanism containing section for containing the rotation mechanism of the scanning section 168.

Figure 15:
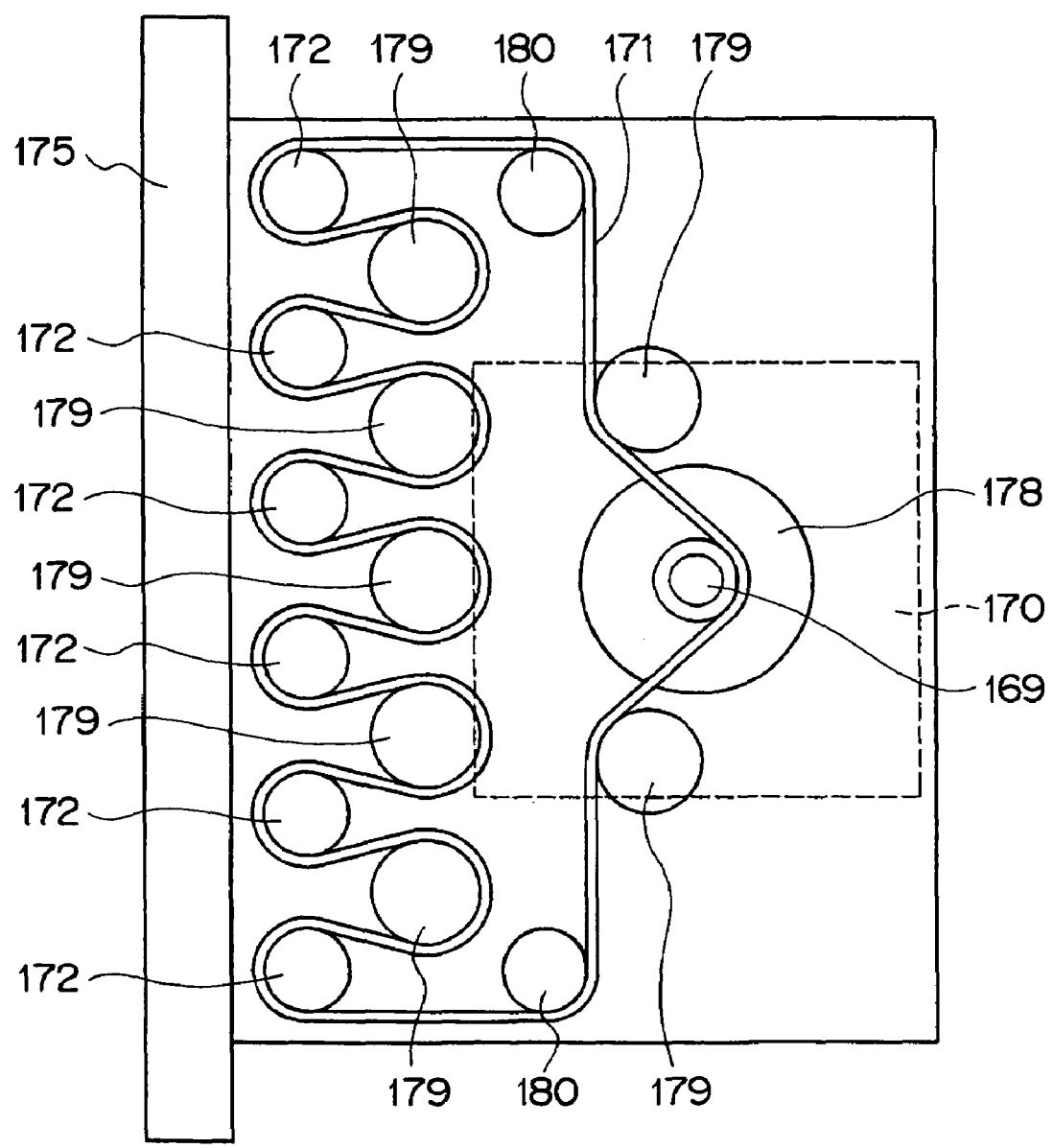
FIG. 15 is a sectional view on A-A of FIG. 13.

FIG. 15 shows the interior of the rotation mechanism containing section 177. In this example, the driving force of the motor 178 contained inside the motor containing section 170 is transmitted to the nozzle section 157 by means of the belt mechanism. The toothed pulley 169 is provided on the rotation shaft of the motor 178. The belt 171 is spanned between the toothed pulley 169, and the toothed pulleys 172 provided on the six sets of nozzle sections 157, via seven rollers 179 and two toothed pulleys 180. The rotation mechanism may be constructed by a combination of gears instead of the belt mechanism.

Figure 16:
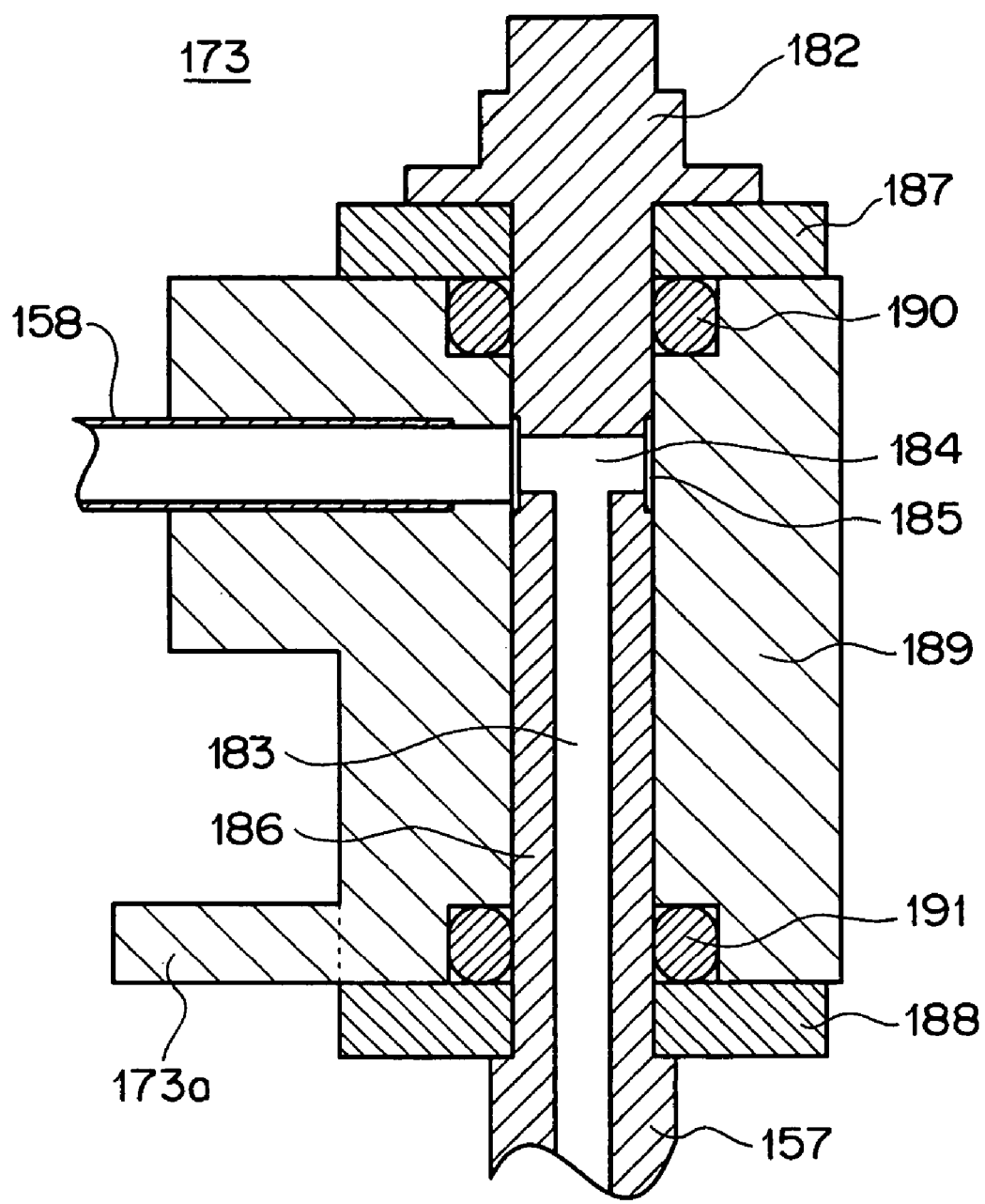
FIG. 16 is an enlarged sectional view of part of FIG. 13.

FIG. 16 shows in detail a section of the upper end portion 173 of the nozzle section 157. The upper end region 173 has a tip portion 182 having a rim protruding radially from the nozzle section 157, a transverse cavity 184 extending in the transverse direction and communicated with a longitudinal cavity 183 extending in the longitudinal direction inside the nozzle section 157, and an annular groove 185 provided annularly around the periphery passing an opening section of the transverse cavity 184. This annular groove 185 is provided in order to smoothly pass air from the cylinder 164 through the circular tube 158. At the upper end portion 173 of the nozzle section 157, the outer diameter of the nozzle section 157 is formed slightly thinner than the outer diameter of the other regions, and is rotatably supported with respect to the circular tube support section 189 which supports the circular tube 158, via bearings 187 and 188. Here the circular tube support section 189 does not rotate with rotation of the nozzle section 157, but moves with movement of the nozzle section 157 in the vertical direction. Reference symbols 190 and 191 denote O-rings.

Next is a description of the operation of the device according to the embodiments.

In the six sets of pipette sections 156, there is respectively contained integrated carriers (not shown in the figure). The device for containing, reacting and measuring 155 including the pipette sections 156 can be moved as a whole in the X, Y and Z axis directions. This is moved to a plurality of containers which contain a predetermined reagent, and the small diameter portions 162 of the pipette sections 156 are inserted into the containers. Then for the liquid such as the contained reagent, drawing and discharging of the liquid via the inlet/outlet 161 is performed by rotating the motor 167 of the drawing and discharging section 159 to rotate the ball screw 155 via the coupler 166, to vertically move the cylinder rods 164 contained inside the cylinder block 164a and attached to the nut section threaded onto the ball screw 165, so that air flows into and is discharged from the pipette sections 156 through the circular tube 158, the transverse cavity 184, the annular groove 185 and the longitudinal cavity 183. By so doing, the integrated carrier and the liquid contained in the large diameter section 163 are brought into contact to perform the reaction process. When the small diameter portion 162 is inserted into the container, the inlet/outlet 161 contacts the bottom of the container, and when the pipette section 156, and hence the nozzle section 157 mounted on the pipette section 156 moves the small distance d, the grounding is detected by the grounding sensor 176, so that movement in the downward direction by the moving section is stopped, and the drawing/discharging operation is then performed.

When the necessary processing has been completed, and measuring is performed taking the light emission due to the fluorescent substance being the target substance, which is produced by the integrated carrier, the pipette section 156 of the device for containing, reacting and measuring 155 is moved as far as the predetermined position of the light receiving section and the irradiating section of the measuring device body, and scanning for measurement is performed by the scanning section 168 by rotating and driving the nozzle section 157. Scanning by means of this scanning section 168 involves rotationally driving the motor 178 to rotate the toothed pulley 169 provided on the rotation shaft of the motor 178, and thus rotationally drive each of the six sets of respective nozzle sections 157 by means of the belt 171 spanned between the toothed pulley 169 and the toothed pulleys 172 and the like. At the same time, the excitation light from the irradiating section is irradiated onto the integrated carrier and the generated fluorescence is measured.

The above described respective embodiments have been described in detail to further explain the present invention, and in no way preclude other embodiments. Consequently the embodiments can be altered provided the gist of the invention is retained. For example, with each of the embodiments, the description was only for the case where oligonucleotides were used as the detection substance. However the invention is not limited to this case, and for example not only other genetic material but also immunity substances, amino acids, proteins, sugars and so forth may be used. Furthermore, in the first embodiment, the description was for the case where a pump was used as the drawing and discharging section. However the invention is not limited to this case, and for example this may comprise a cylinder and piston.

Moreover, in the above description, the case where fluorescence was measured as the measurement device was described. However the case of chemiluminescence, or measurement of electromagnetic waves of various wavelengths is also possible. For example, the case of measuring wavelength ranges of electromagnetic waves of for example infrared rays, ultraviolet rays, X-rays, radio waves and so forth outside of the visual light, as the electromagnetic waves is also possible.

Furthermore, in the above description, only the case where each pipette section or slender tube was one set was described. However the invention is not limited to this case, and for example a case where another set of pipette sections or slender tubes are provided in rows is also possible. Moreover, needless to say, the numerical values used in the above description are only for example, and are not limiting to the invention. Furthermore, the various components constituting the device for containing, reacting and measuring described in the various embodiments may be optionally selected and suitably modified and combined to thereby make up new apparatus for containing, reacting and measuring. The laser beam from the laser device may be irradiated so as to scan the integrated carrier in the longitudinal direction using a polygon mirror, and then be received.

Furthermore, by providing two light receiving sections for receiving light from different directions at different positions, on the measuring device body, stereoscopic vision is possible. As a result, the fixed positions can be made three dimensional. Therefore a high density integrated carrier which is integrated in multi layers can also be measured more accurately. In this case, due to the distance between the respective light receiving sections, and the angle of the measuring direction of the respective light receiving sections, it is possible to detect differences in the distance in the depth direction thereof.

Moreover, in the case of measuring by rotating the container section, then as a measurement positioning section for preventing rotation swing, for example a guide member for guiding the rotation may be provided near the measurement position, for example in the groove section 102a, so as to contact the outer peripheral face of the container section (pipette section), for example the outer peripheral face of the large diameter section or the small diameter section, at one place, or so as to contact between a plurality of places, or to contact the whole periphery. Furthermore, a mechanism may be provided coupled to the container section itself, for rotationally driving the container section.

The invention claimed is:

1. A method of containing, reacting and measuring comprising:

a containing step for containing in a transparent container section, an integrated carrier having a base member of a long slender shape such as a filament, a braid or a tape with several kinds of substances for detection having predetermined chemical structures fixed thereto at predetermined spacing along the longitudinal direction thereof, and with each of the chemical structures associated with their fixed positions, wound on a carrier in a condition where this can be measured from the outside;

a reaction step for drawing a liquid suspending a labeled bonding substance which is capable of bonding with said substance for detection, to inside said container section, and immersing said integrated carrier in the liquid to react said bonding substance with said substance for detection;

a measurement preparation step for removing said bonding substances which have not contributed to the reaction and said liquid; and a measurement step for measuring light from the base member contained in said container section.

2. A method of containing, reacting and measuring according to claim 1, wherein said measuring step scans all fixed positions of said integrated carrier by rotating said container section.

3. A method of containing, reacting and measuring according to claim 1, wherein in said measurement preparation step, there is included a step for drawing measurement liquid after removing said bonding substances which have not contributed to the reaction and liquid suspending these, and said measurement step measures in a condition with said integrated carrier immersed in the measurement liquid.

4. A method of containing, reacting and measuring according to claim 3, wherein said reaction step is performed by moving the nozzle section with said container section mounted thereon to the position of a container which contains an appropriate reagent, and drawing up this reagent, and said measurement step is performed by moving said nozzle section as far as the position where said light receiving section is provided.

5. A method of containing, reacting and measuring according to claim 1, wherein in said reaction step, said container section or the liquid which is drawn into said container section is shaken, or drawing and discharging of the liquid is repeated.

\* \* \* \* \*